United States Patent
Yoshida et al.

(10) Patent No.: US 9,346,036 B2
(45) Date of Patent: May 24, 2016

(54) OXIDE CATALYST

(75) Inventors: Jun Yoshida, Tokyo (JP); Tatsuo Yamaguchi, Tokyo (JP); Kenji Izumiyama, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 89 days.

(21) Appl. No.: 14/129,260

(22) PCT Filed: Jun. 13, 2012

(86) PCT No.: PCT/JP2012/065139
§ 371 (c)(1),
(2), (4) Date: Mar. 4, 2014

(87) PCT Pub. No.: WO2013/002029
PCT Pub. Date: Jan. 3, 2013

(65) Prior Publication Data
US 2014/0171303 A1    Jun. 19, 2014

(30) Foreign Application Priority Data

Jun. 28, 2011 (JP) .................................. 2011-143284

(51) Int. Cl.
*B01J 23/887* (2006.01)
*B01J 37/02* (2006.01)
(Continued)

(52) U.S. Cl.
CPC ............ *B01J 23/8876* (2013.01); *B01J 35/002* (2013.01); *B01J 37/0236* (2013.01); *C07C 45/35* (2013.01); *B01J 37/0018* (2013.01);
(Continued)

(58) Field of Classification Search
CPC .. B01J 23/8876; B01J 37/0236; B01J 35/002; B01J 37/08; B01J 37/0018; B01J 2523/00; B01J 37/0045; C07C 45/35
See application file for complete search history.

(56) References Cited

U.S. PATENT DOCUMENTS

| 4,001,317 A | 1/1977 | Grasselli et al. |
| 5,728,894 A | 3/1998 | Nagano et al. |

(Continued)

FOREIGN PATENT DOCUMENTS

| EP | 1 459 803 A1 | 9/2004 |
| JP | 2000-237592 A | 9/2000 |

(Continued)

OTHER PUBLICATIONS

English translation of International Preliminary Report on Patentability and Written Opinion mailed Jan. 16, 2014, in PCT Intematonal Application No. PCT/JP2012/065139.
(Continued)

*Primary Examiner* — Anthony J Zimmer
(74) *Attorney, Agent, or Firm* — Birch, Stewart, Kolasch & Birch, LLP

(57) ABSTRACT

An oxide catalyst for use in an oxidation reaction of an olefin and/or an alcohol, the oxide catalyst comprising: the oxide catalyst contains molybdenum, bismuth, iron, cobalt, and cerium; an atomic ratio a of bismuth to 12 atoms of molybdenum is $2 \leq a \leq 6$, an atomic ratio b of iron to 12 atoms of molybdenum is $2.5 < b \leq 5$, an atomic ratio c of cobalt to 12 atoms of molybdenum is $2 \leq c \leq 8$, an atomic ratio d of cerium to 12 atoms of molybdenum is $0.5 \leq d \leq 6$, and an atomic ratio of iron/cobalt is $0.4 \leq b/c \leq 2.5$; wherein when a spacing d of a complex oxide of cerium and molybdenum showing a peak at 33.50° in a X-ray diffraction is taken as a reference, a change rate of d is 5000 to 9000 ppm.

4 Claims, 2 Drawing Sheets

X-ray diffraction, enlarged view of X-ray diffraction angle 2q=32.5 to 35°

(51) Int. Cl.
B01J 35/00 (2006.01)
C07C 45/35 (2006.01)
B01J 37/08 (2006.01)
B01J 37/00 (2006.01)

(52) U.S. Cl.
CPC .............. *B01J37/0045* (2013.01); *B01J 37/08* (2013.01); *B01J 2523/00* (2013.01)

(56) References Cited

U.S. PATENT DOCUMENTS

| | | |
|---|---|---|
| 6,583,316 B1 | 6/2003 | Onodera et al. |
| 2005/0032639 A1* | 2/2005 | Watanabe .............. B01J 23/002 502/302 |
| 2008/0019892 A1 | 1/2008 | Neto et al. |
| 2011/0077148 A1 | 3/2011 | Kano et al. |

FOREIGN PATENT DOCUMENTS

| | | |
|---|---|---|
| JP | 2001-25664 A | 1/2001 |
| JP | 2008-502567 A | 1/2008 |
| JP | 2010-172651 A | 8/2010 |
| JP | 2011-72909 A | 4/2011 |
| WO | WO 95/35273 A1 | 12/1995 |

OTHER PUBLICATIONS

International Search Report mailed Sep. 11, 2012, in PCT International Application No. PCT/JP2012/065139.
European Search Report issued Jun. 6, 2014, in European Patent Application No. 12804529.1.

\* cited by examiner

X-ray diffraction, enlarged view of X-ray diffraction angle 2q=32.5 to 35°

OXIDE CATALYST

TECHNICAL FIELD

The present invention relates to an oxide catalyst used in an oxidation reaction of an olefin and/or an alcohol.

BACKGROUND ART

As a method for producing methyl acrylate or methyl methacrylate according to an oxidative esterification reaction using at least one selected from propylene, isobutylene, and t-butyl alcohol as a starting material, and an unsaturated aldehyde as an intermediate, there are known two methods: a method referred to as the "direct metha process" including two reaction steps; and a method referred to as the "direct oxidation process" including three reaction steps. According to "Sekiyu Kagaku Purosesu (Petrochemical Processes)" (edited by the Japan Petroleum Institute, pages 172 to 176, Kodansha Scientific, Ltd.), the direct oxidation process is a process for producing methyl acrylate or methyl methacrylate in three steps. The first oxidation step is a step of subjecting at least one starting material selected from propylene, isobutylene, and t-butanol to a gas-phase catalytic oxidation reaction with molecular oxygen in the presence of a catalyst, to produce acrolein or methacrolein. The second oxidation step is a step of subjecting the acrolein or the methacrolein obtained in the first oxidation step to a gas-phase catalytic oxidation reaction with molecular oxygen in the presence of a catalyst, to produce an acrylic acid or a methacrylic acid. An esterification step is a step of further subjecting the acrylic acid or the methacrylic acid obtained in the second oxidation step to esterification, when using methanol as an alcohol, to obtain methyl acrylate or methyl methacrylate. Meanwhile, the direct metha process contains two catalytic reaction steps, wherein the first reaction step includes subjecting propylene or isobutylene and/or t-butanol as a starting material(s) to a gas-phase catalytic oxidation reaction with a molecular oxygen-containing gas to produce acrolein or methacrolein, and the second reaction step includes reacting the obtained acrolein or methacrolein, for example, methanol as an alcohol, and molecular oxygen, to produce methyl acrylate or methyl methacrylate in one step.

A catalyst found years ago by Sohio Company has existed as a catalyst for producing an unsaturated aldehyde as a main component. Thereafter, many complex oxide catalysts containing Mo and Bi as essential components have been reported. For example, a catalyst focusing on Mo, Bi, Ce, K, Fe, Co, Mg, Cs, and Rb as metals contained in the catalyst is described in Patent Document 1. Catalysts for producing an unsaturated aldehyde and an unsaturated acid are described also in Patent Document 2. Among them, a catalyst represented by $Sb_{0.5}Cs_{0.5}S_{0.25}Ni_{2.5}Co_{4.5}Fe_4Bi_1Mo_{12}O_x$ provides the maximum per-pass yield.

LIST OF PRIOR ART

Patent Document

Patent Document 1: International Publication No. WO95/35273
Patent Document 2: U.S. Pat. No. 4,001,317

SUMMARY OF INVENTION

Problems to be Solved by the Invention

The productivity of the oxidation reaction described above is largely influenced by a starting material concentration and a reaction temperature. It is theoretically considered that the productivity is improved as the starting material concentration is higher and the reaction temperature is higher. However, in fact, when the reaction temperature and the starting material concentration are set to be excessively high, the problem of rather reduced productivity is caused.

For example, when an unsaturated aldehyde is obtained by a gas-phase catalytic oxidation reaction, if the starting material concentration is high, an oxygen partial pressure required by generation of heat is increased, which increases the generation of a successive oxide. Therefore, the selectivity of the unsaturated aldehyde is significantly decreased, which remarkably decreases the productivity. Meanwhile, if the reaction temperature is about 350° C. to 370° C., the selectivity of the unsaturated aldehyde is increased. However, if the reaction temperature is 370° C. or more, the selectivity of the unsaturated aldehyde is significantly decreased, which remarkably decreases the productivity. Therefore, there is desired a catalyst showing high productivity of a desired product even under the reaction conditions of high starting material concentration and high reaction temperature.

In the above viewpoints, an oxide catalyst of a bismuth-molybdenum (Bi—Mo) system utilized in the art, and an oxide catalyst of a system in which iron, cerium or the like is further added to a bismuth-molybdenum system, as described in Patent Document 1 have been investigated. As a result, it has been found that, in such a catalyst, all metals are not complexed, and the metals exist also as $Bi_2Mo_3O_{12}$, $Ce_2Mo_3O_{12}$, $Fe_2Mo_3O_{12}$, $Bi_2O_3$, $Fe_2O_3$, and $CeO_2$ from X-ray structural analysis or the like. These single-component oxides or the two-component oxides have a comparatively high oxidizing ability, and therefore generates the successive oxide which is in a state where the desired product is further oxidized, to cause the problem of reduced productivity of the desired product.

Then, the present inventors have, as a result of devoted examinations to optimize the oxidizing ability of the catalyst, found out that the ratios of Mo, Bi, Fe, Co, and Ce in the catalyst are optimized and the generation of uncomplexed components of these components is suppressed to suppress the generation of the successive oxides, improving the productivity of the desired product.

Thus, the inventors conceived the present invention.

That is, the present invention is as follows.

[1]

An oxide catalyst for use in an oxidation reaction of an olefin and/or an alcohol, the oxide catalyst comprising:

the oxide catalyst contains molybdenum, bismuth, iron, cobalt, and cerium; an atomic ratio a of bismuth to 12 atoms of molybdenum is 2≤a≤6, an atomic ratio b of iron to 12 atoms of molybdenum is 2.5<b≤5, an atomic ratio c of cobalt to 12 atoms of molybdenum is 2≤c≤8, an atomic ratio d of cerium to 12 atoms of molybdenum is 0.5≤d≤6, and an atomic ratio of iron/cobalt is 0.4≤b/c≤2.5;
wherein when a spacing d of a complex oxide of cerium and molybdenum showing a peak at 33.50° in a X-ray diffraction is taken as a reference, a change rate of d is 5000 to 9000 ppm.

[2]

The oxide catalyst according to item [1] above, wherein the oxide catalyst has a composition represented by the following composition formula (1):

$$Mo_{12}Bi_aFe_bCo_cCe_dA_eB_fO_g \qquad (1),$$

wherein Mo represents molybdenum; Bi represents bismuth; Fe represents iron; Co represents cobalt; Ce represents cerium; A represents at least one element selected from the group consisting of cesium and rubidium; B represents at least one element selected from the group consisting of copper, nickel, magnesium, and lead; a to f represents an atomic ratios of each element to 12 atoms of Mo; 2≤a≤6, 2.5<b≤5, 2≤c≤8, 0.4≤b/c≤2.5, 0.5≤d≤6, 0.01≤e≤2, and 0≤f<2 are satisfied; and g represents number of oxygen atoms determined by a valence of a constituent element other than oxygen.

[3]

A method for producing the oxide catalyst according to item [1] or [2] above, the method comprising the steps of:

aging a starting material slurry comprising molybdenum, bismuth, iron, cobalt, and cerium at a temperature higher than room temperature;

drying the aged starting material slurry;

preliminarily calcining the dried product at 120° C. or more and 350° C. or less; and subsequently finally calcining the preliminarily calcined product at a temperature of 400° C. or more and 700° C. or less.

[4]

A method for producing an unsaturated aldehyde comprising the step of oxidizing at least one olefin selected from the group consisting of propylene and isobutylene and/or t-butyl alcohol using the oxide catalyst according to item [1] or [2].

Advantageous Effects of Invention

The present invention can provide the catalyst providing high productivity of the desired product under reaction conditions of a high starting material concentration and a high reaction temperature in the oxidation reaction of the olefin and/or the alcohol.

MODE FOR CARRYING OUT THE INVENTION

Figure 1:
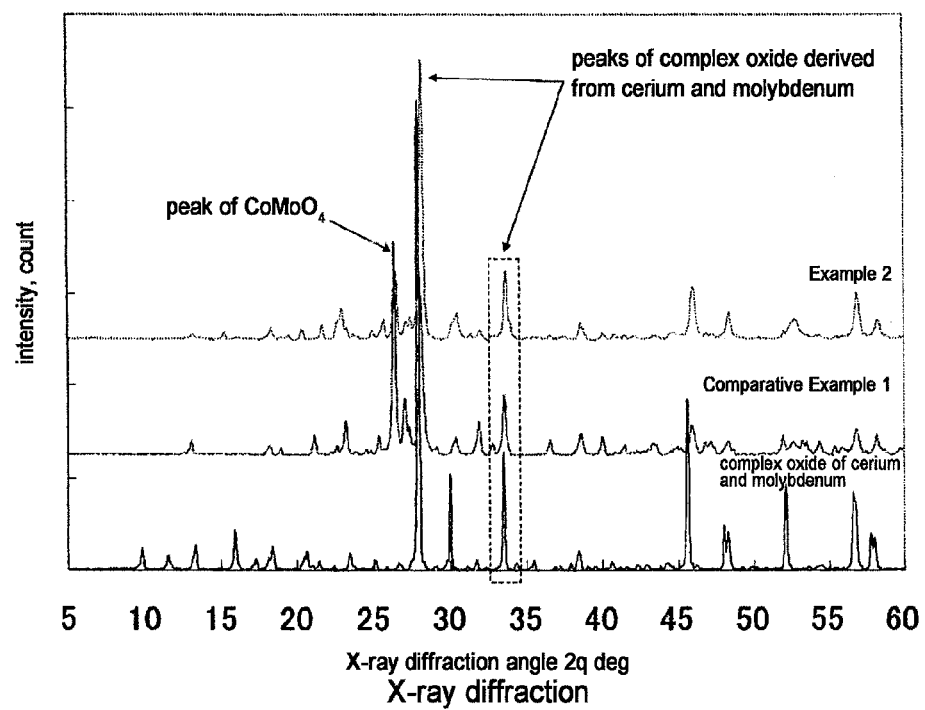
FIG. 1 shows X-ray diffraction peaks of oxide catalysts in Example 2 and Comparative Example 1.

Hereinafter, a mode for carrying out the present invention (hereinafter, referred to as the "present embodiment") will be described in detail. However, the present invention is not limited to the following embodiments, and can be variously modified within the scope of the spirit of the invention.

[1] Oxide Catalyst for Oxidation Reaction

An oxide catalyst according to the present embodiment is an oxide catalyst for use in an oxidation reaction of an olefin and/or an alcohol, the oxide catalyst comprising:

the oxide catalyst contains molybdenum, bismuth, iron, cobalt, and cerium; an atomic ratio a of bismuth to 12 atoms of molybdenum is 2≤a≤6, an atomic ratio b of iron to 12 atoms of molybdenum is 2.5<b≤5, an atomic ratio c of cobalt to 12 atoms of molybdenum is 2≤c≤8, an atomic ratio d of cerium to 12 atoms of molybdenum is 0.55≤d≤6, and an atomic ratio of iron/cobalt is 0.4≤b/c≤2.5;

wherein when a spacing d of a complex oxide of cerium and molybdenum showing a peak at 33.50° in a X-ray diffraction is taken as a reference, a change rate of d is 5000 to 9000 ppm.

The selectivity of a desired product and the suppression of successive oxidation contribute to an improvement in the productivity of the desired product. The present inventors considered that the complex oxide having a structure in which the change rate of the spacing d is 5000 to 9000 ppm contributes to the stability of an intermediate. Oxidative hydrogen elimination generates a π allyl intermediate from the olefin and/or the alcohol. Furthermore, an addition reaction or a dehydrogenation reaction changes the π allyl intermediate, to obtain the desired product. The π allyl intermediate has high reactivity and is unstable, and thereby the π allyl intermediate is immediately changed or decomposed to the other compound in normal circumstances. However, it is considered that the oxide catalyst according to the present embodiment controls the stability of the π allyl intermediate and a reaction to obtain the desired product advantageously proceeds. When oxygen is added to the π allyl intermediate, the π allyl intermediate is changed to an aldehyde or a carboxylic acid. When ammonia is added to the π allyl intermediate, the π allyl intermediate is changed to a nitrile. When hydrogen is eliminated from the π allyl intermediate, a double bond is formed and an olefin is obtained from an alcohol, and a diolefin or the like is obtained from the olefin. Therefore, various desired products can be obtained using the oxide catalyst according to the present embodiment by appropriately selecting a starting material supplied to a reactor.

Although the reason why the oxide catalyst according to the present embodiment suppresses the generation of a successive oxide is unclear, the present inventors carried out investigation, and revealed that the successive oxide is decreased even if the desired product was an unsaturated aldehyde. The unsaturated aldehyde is a compound which is apt to be extremely easily oxidized. As a surprising result, the successive oxide derived from the unsaturated aldehyde is decreased even under conditions of a high starting material concentration and a high reaction temperature. If even for the unsaturated aldehyde which is apt to be oxidized a successive oxidation reaction can be suppressed, it is considered that the generation of successive oxide is also suppressed for other desired products. The successive oxide is a byproduct which is not preferable in all the oxidation reactions. If the generation of the successive oxide can be suppressed, the significant improvement in the productivity can be expected.

In the present specification, the successive oxide means a compound in a state where the desired product is further oxidized. Therefore, an unsaturated carboxylic acid is considered as a kind of successive oxide when the desired product is the unsaturated aldehyde such as a first reaction step of the direct metha process. Other examples of the successive oxide may include carbon dioxide, peroxides, diketones, and epoxy compounds.

(1) Composition

In the oxide catalyst according to the present embodiment, from the viewpoint of complexing metal elements in a Mo—Bi system metal oxide, Mo, Bi, Ce, and Fe indispensably exist. The atomic ratio a of Bi to 12 atoms of Mo is set to 2≤a≤6. From the viewpoint of further enhancing the selectivity of the desired product, the atomic ratio a is preferably 2≤a≤5, and more preferably 2≤a≤4. In the same viewpoint, the atomic ratio d of Ce is 0.5≤d≤6, preferably 1≤d≤5, and more preferably 1≤d≤4. Bi and Mo are likely to form complex oxides such as $Bi_2Mo_3O_{12}$ and $Bi_2MoO_6$ which are active species in a gas-phase catalytic oxidation and ammoxidation reactions or the like, and have high catalytic activity. However, Bi and Mo have a low melting point and low heat resistance. Meanwhile, it is difficult for Ce and Mo to form a complex oxide such as $Ce_2Mo_3O_{12}$. However, Ce and Mo have a high melting point and very high heat resistance. If the two are appropriately complexed, a Ce—Bi—Mo—O system complex oxide is formed, which has a complexed structure where Bi is solid-dissolved in $Ce_2Mo_3O_{12}$ having high heat resistance and has high activity and heat resistance.

From the viewpoint of enhancing the catalytic activity without decreasing the selectivity of the desired product, Fe is an essential element in order to industrially synthesize the desired product as in Mo and Bi. However, when the content of Fe is increased, $Fe_2O_3$ is generated, and the successive oxide such as CO and $CO_2$ tends to be increased. As a result, the selectivity of the desired product is decreased. Even if the content of Fe is increased, $Fe_2O_3$ is not be generated in some cases. However, a complex oxide of a two-component system, Fe—Mo—O, is generated at this time. This is an inactive component showing no catalytic activity. Therefore, conventionally, the atomic ratio of Fe to 12 atoms of Mo has been generally set to 0<Fe≤2.5 in order to exhibit a high yield. There has been no idea for increasing the atomic ratio of Fe to 2.5 or more to generate an effective crystal phase. Meanwhile, the present inventors found out that a high-performance crystal structure of the four-component system, Ce—Bi—Fe—Mo—O system, is formed by increasing not only the content of Fe but also the contents of Bi and Ce in a composition region beyond the upper limit of the atomic ratio of Fe which is the conventional common general knowledge. The present inventors presume that the oxide catalyst having a crystal of the Ce—Bi—Fe—Mo—O system exhibits the high yield of the desired product because Mo—O bond energy of a Bi—O—Mo bond of the complex oxide such as $Bi_2Mo_3O_{12}$ and $Bi_2MoO_6$ containing Ce and Fe as active species is suitable. The atomic ratio b of Fe to 12 atoms of Mo of the oxide catalyst according to the present embodiment is 2.5<b≤5, preferably 2.5<b≤4.5, and more preferably 2.5<b≤4.

In the oxide catalyst according to the present embodiment, Co is an essential element in order to industrially synthesize the desired product as in Mo, Bi, and Fe. Co forms a complex oxide $CoMoO_4$. Co serves as a carrier for highly dispersing active species such as Bi—Mo—O, and serves to incorporate oxygen from a gas phase and supply it to Bi—Mo—O or the like. In order to obtain the unsaturated aldehyde in a high yield, it is necessary to complex Co with Mo, to form the complex oxide $CoMoO_4$. From the viewpoint of reducing the formation of a single-component oxide such as $Co_3O_4$ and CoO, the atomic ratio c of Co is 2≤c≤8, preferably 2.5≤c≤6, and more preferably 2.5≤c≤4. From the viewpoint of enhancing the activity of the catalyst, the atomic ratio b/c of Fe and Co is 0.4≤b/c≤2.5, preferably 0.7≤b/c≤2.0, and more preferably 1≤b/c≤1.5.

The oxide catalyst according to the present embodiment preferably has a composition represented by the following composition formula (1):

$$Mo_{12}Bi_aFe_bCo_cCe_dA_eB_fO_g \qquad (1),$$

wherein Mo represents molybdenum; Bi represents bismuth; Fe represents iron; Co represents cobalt; Ce represents cerium; A represents at least one element selected from the group consisting of cesium and rubidium; B represents at least one element selected from the group consisting of copper, nickel, magnesium, and lead; a to f represents atomic ratio of each element to 12 atoms of Mo; 2≤a≤6, 2.5<b≤5, 2≤c≤8, 0.4≤b/c≤2.5, 0.5≤d≤6, 0.01≤e≤2, and 0≤f<2 are satisfied; and g represents number of oxygen atoms determined by a valence of a constituent element other than oxygen.

In the above-mentioned composition formula (1), A represents cesium and/or rubidium, and it is considered that A plays the role of neutralizing the acid site of $MoO_3$ or the like which is not complexed, by a catalyst for producing the unsaturated aldehyde. Whether cesium and/or rubidium are/is contained does not influence the crystal structure of Ce—Bi—Fe—Mo—O to be described later. The atomic ratios of these elements to 12 atoms of Mo are 0.01≤e≤2 from the viewpoint of the catalytic activity. The atomic ratio e of A is adjusted to this numerical range because the catalyst is basic when the amount of an alkali element is increased to the range or more, and the olefin or the alcohol as a starting material is hardly adsorbed onto the catalyst, which tends to disable sufficient exhibition of the catalytic activity.

B represents at least one element selected from the group consisting of copper, nickel, magnesium, and lead. It is considered that the element is partially substituted for cobalt in the oxide. Copper has the role of improving the activity of the catalyst. However, from the viewpoint of maintaining a balance with the generation of a Ce—Bi—Fe—Mo—O crystal exhibiting catalyst performance, the upper limit of the atomic ratio f of B is preferably f<2. When the atomic ratio is f<2, nickel, magnesium, and lead have the role of stabilizing the crystal structure of $CoMoO_4$ to suppress a phase transition or the like according to a pressure and a temperature. Because the element represented by B improves the activity of the catalyst or stabilizes the crystal structure of $CoMoO_4$ in the catalyst, the element does not influence the crystal structure of Ce—Bi—Fe—Mo—O, and is positioned as an optional component whose content may be zero (f=0).

Even if the elements represented by A and B are contained or are not contained in the catalyst, a crystal structure aside from the crystal structure of Ce—Bi—Fe—Mo—O to be described later is formed, and thus the elements do not influence the crystal structure of Ce—Bi—Fe—Mo—O.

The oxide catalyst having the composition represented by the above-mentioned composition formula (1) is characterized in that the selectivity of the unsaturated aldehyde is high. The oxide catalyst is suitably used in the first reaction step of the direct metha process. Because the last oxidation product is the unsaturated carboxylic acid in the direct oxidation process, the direct oxidation process has a small merit of reducing a methacrylic acid in a step of obtaining the unsaturated aldehyde as the intermediate. Thus as the total yield of methacrolein and methacrylic acid is higher, the catalyst can be said to be desirable. Meanwhile, because the direct metha process generates the unsaturated aldehyde in the first reaction step, and thereafter generates an unsaturated carboxylic acid ester from the unsaturated aldehyde in the second reaction step, a step of generating the unsaturated carboxylic acid as the desired product does not exist. Therefore, in an oxidation process with the complex oxide catalyst, only the unsaturated aldehyde is desirably generated, and the generation of the unsaturated carboxylic acid is desirably suppressed as much as possible. That is, when aiming at optimizing the catalyst for the first reaction step of the direct metha process, a catalyst is desirable, which has directivity distinctly different from that of the catalyst for the direct oxidation process, provides the high yield of the unsaturated aldehyde as the desired product, and the low yield of the unsaturated carboxylic acid as the successive oxide.

(2) Crystal Structure

When the range of an X-ray diffraction angle 2θ=5° to 60° is measured by the X-ray diffraction (XRD), an oxide containing only cerium and molybdenum shows a peak at 33.50°. If iron and bismuth are further complexed with the oxide containing only cerium and molybdenum, a shift of the peak takes place. Because the oxide catalyst according to the present embodiment contains the oxide containing cerium and molybdenum, and a metal obtained by complexing iron with bismuth, the oxide catalyst shows a peak not at 33.50° but at 33.50°+α° (0<α).

When, according to the Braggs condition formula ("Kotai Hyoumen Kyarakutarizeshon no Jissai (Actual Conditions of Solid Surface Characterization)", edited by Yasuhiro Tanaka and Hiromi Yamashita, pages 13 to 25, Kodansha Scientific, Ltd.), a spacing d between crystal faces, an incident angle and reflection angle θ of X-rays to the crystal face, and a wavelength λ have a relationship of the following formula (II):

$$2d \sin θ = nλ \quad (n: \text{integer}) \quad (II),$$

that is, when the path difference between incident and scattered X-rays is equal to the integral multiple of the wavelength of the incident X-rays, a diffraction phenomenon is observed. In the present embodiment, primary reflection is set, and diffraction satisfying a reflective condition of n=1 is set. For example, when an element is solid-dissolved by substitution in a multicomponent system complex oxide, and the X-ray diffraction angle (2θ) shifts to a lower angle side, the spacing d is in a state of spreading. When the X-ray diffraction angle (2θ) shifts to a higher angle side, the spacing d is in a state of being shortened. For this reason, the shift of the peak appearing at 33.50° in XRD to the higher angle side (0<α) means a change in the spacing d in a state of the spacing d of the oxide being shortened by the complexation of the metals.

The change rate of the spacing d is represented by the following formula (III):

$$d \text{ change rate [ppm]} = (d^0 - d')/d^0 \times 1000000 \quad (III)$$

wherein $d^0$ represents a spacing of the complex oxide of cerium and molybdenum showing a peak at 33.50°, and d' represents a spacing of the oxide catalyst according to the present embodiment. In the oxide catalyst according to the present embodiment, the change rate of d is 5000 to 9000 ppm. Because an oxide close to the two-component system of cerium and molybdenum is contained when the change rate of d is less than 5000 ppm, the oxide catalyst has a high oxidizing ability and when the oxide catalyst is used as the catalyst, the yield of the successive oxide is increased. Meanwhile, when the change rate is more than 9000 ppm, the activity is decreased. From the viewpoint of obtaining the desired product in high activity and a high yield, the change rate of d is more preferably 5500 to 8500 ppm, and still more preferably 6000 to 8000 ppm.

A mechanism in which the spacing d changes is not clear. However, it is considered that this is because Fe is further solid-dissolved in the complex oxide of Ce, Bi, and Mo, to newly form a high-performance crystal structure of the complexed four-component system Ce—Bi—Fe—Mo—O. A method for producing a catalyst for dispersing and complexing Bi or the like will be described in detail later. However, the abundance ratio of the metal is also important in order to form such a crystal structure. When the atomic ratio b of Fe to 12 atoms of Mo satisfies the range of 2.5<b≤5, the crystal structure is generated. However, when the atomic ratio b is less than 2.5, the crystal structure is not generated, or even when the crystal structure is generated, the amount of the crystal structure is extremely small and it is difficult for the obtained oxide catalyst to suppress the generation of the successive oxide. That is, when the atomic ratio b is b≤2.5, the yield of the successive oxide is increased. When the atomic ratio b is b>5, the yield of $CO_x$ ($CO_2$ and CO or the like) is increased. As a result, the productivity of the desired product is decreased.

As the complexation index of Ce—Bi—Fe—Mo—O, the shift of 33.50° is desirably taken as a reference. However, the influence caused by complexation takes place also for the other peaks. The oxide catalyst according to the present embodiment has peaks at X-ray diffraction angles (2θ) of 28.17°+0.05°, 33.50°+α°, and 26.44°±0.05° in a descending order of intensities. Among them, the two peaks of 28.17°±0.05° and 33.50°+α° are mainly derived from Ce—Mo—O, and the peak of 26.44°±0.05° is mainly derived from Co—Mo—O. From the viewpoint of suppressing the generation of the successive oxide, the intensity of each of the peaks is preferably decreased according to the above-mentioned order.

As for the peak of the X-ray diffraction angle (2θ)=33.50°+α°, α represents the shift of the peak from 33.50°. When the change rate of d is 5000 to 9000 ppm, 0.10°≤α≤0.25° is set.

(3) Components Other than Metal Oxide

The oxide catalyst for the oxidation reaction according to the present embodiment may contain a carrier for supporting a metal oxide. The catalyst containing the carrier is preferable in that the catalyst provides the high dispersion of the metal oxide and provides high wear resistance to the supported metal oxide. Herein, when the catalyst is molded by an extrusion molding method, the catalyst preferably contains the carrier. However, when methacrolein is produced in a fixed-bed reactor, and the catalyst is molded into tablets, the catalyst may not contain the carrier. Examples of the carrier may include, but not particularly limited to, silica, alumina, titania, and zirconia. Generally, silica itself is more inactive than the other carriers, and has a good bind action to the metal oxide without reducing the selectivity to the desired product, which is therefore a preferable carrier. Furthermore, the silica carrier is also preferable in that it is likely to provide high wear resistance to the supported metal oxide. When the catalyst is molded by the extrusion molding method, the content of the carrier based on the whole catalyst is preferably 5 to 10% by mass.

Also in the case of the catalyst used in a fluid bed reactor, from the same viewpoint as the above, silica is preferably used as the carrier. From the viewpoint of optimizing the influence of Ce—Bi—Fe—Mo—O to the crystal structure and an apparent specific gravity to improve flowability, the content of the carrier in the catalyst is preferably 80% by mass or less based on the total mass of the catalyst, more preferably 70% by mass or less, and still more preferably 60% by mass or less. In the case of the catalyst requiring strength for a fluid bed reaction or the like, from the viewpoint of showing practically sufficient crushing resistance and wear resistance or the like, the content of the carrier is preferably 20% by mass or more based on the total mass of the catalyst, more preferably 30% by mass or more, and still more preferably 40% by mass or more.

[2] Method for Producing Catalyst for Oxidation Reaction

As described above, the present inventors have focused on the fact that not a single- and/or two-component system oxide of Ce, Bi, Fe, and Mo but a Ce—Bi—Fe—Mo—O system complex oxide obtained by complexing four components is obtained, and have comprehensively examined the composition ratio and a preparation method thereof.

Because Bi is an essential element for forming active species with Mo, as referred to as a bismuth-molybdenum (Bi—Mo) system catalyst, a large amount of Bi is advantageously contained from the viewpoint of activity. However, when the content of Bi is increased, it is known that the catalyst is heterogeneous. For example, bismuth nitrate as a Bi starting material which is conventionally industrially used is a poorly water-soluble substance. A large amount of nitric acid is required in order to dissolve bismuth nitrate. As a result, a catalyst composition after calcining is heterogeneous, and therefore a conventional catalyst preparation technique has a limitation in an increase in the content of Bi. That is, a single-component oxide such as $Bi_2O_3$ is generated, and a homogeneous catalyst is not obtained, which disadvantageously decreases the productivity of the desired product. From the viewpoint of enhancing the catalytic activity without decreasing the selectivity of the desired product, it has been reported for many years that Fe is an essential element in order to industrially synthesize the desired product as in Mo and Bi. However, as reported in International Publication No. WO95/35273 Pamphlet, a small amount of Fe is optimally added. When the content of Fe is increased, the generation of the successive oxide such as CO and $CO_2$ tends to be increased, which decreases the selectivity of the desired product.

As a result of much trial and error in order to solve the problem, surprisingly, the present inventors have found out that Ce is further added to a catalyst component containing Bi and F more than those of the conventional one, in a catalyst containing a large amount of nitric acid, to suppress the generation of a single oxide for the first time according to a new catalyst production technique satisfying the three requirements of (a) a specific component ratio, (b) a method of aging a specific metal salt slurry, and (c) a specific calcining method, and to newly form a crystal of Ce—Bi—Fe—Mo—O obtained by complexing the four components. Desired complexation has not been generated merely by increasing bismuth nitrate and increasing nitric acid. That is, the present inventors have found out that the contents of Bi and Fe are increased in the catalyst containing a large amount of nitric acid, and Ce is further added to the catalyst, to obtain a crystal structure wherein the four components of Ce—Bi—Fe—Mo—O are compatibilized, for the first time.

That is, only when the three conditions of (a) a specific component ratio, (b) a method of aging a specific metal salt slurry, and (c) a specific calcining method are all met, the crystal structure of the complexed four-component system Ce—Bi—Fe—Mo—O is formed, which enables a catalyst providing the high yield of the unsaturated aldehyde to be obtained. When at least one of the three conditions lacks, the two-component system complex oxide such as Ce—Mo—O, Bi—Mo—O, Fe—Mo—O and Fe—Mo—O, or a single oxide such as $Fe_2O_3$, $Bi_2O_3$, $MoO_3$ and $CeO_2$ is generated, and the range of the change rate of the spacing d also deviates from the range of 5000 to 9000 ppm, which results in the decrease in the yield of the unsaturated aldehyde.

The oxide catalyst according to the present embodiment can be obtained, for example, by a method including a first step of preparing a starting material slurry, a second step of spray-drying the starting material slurry, and a third step of calcining the dried particles obtained in the second step. A preferred aspect of the method for producing the oxide catalyst having the first to third steps will be described later.

(1) Preparation of Starting Material Slurry

In the first step, catalyst starting materials of metal elements contained in the catalyst are mixed to obtain a starting material slurry. Examples of element sources for molybdenum, bismuth, cerium, iron, cobalt, rubidium, cesium, copper, nickel, magnesium, and lead may include an ammonium salt, a nitrate salt, a hydrochloride salt, and an organic acid salt which are soluble in water or nitric acid. The element source may be an oxide, a hydroxide, a carbonate salt, or the like. In the case of the oxide, a dispersion liquid in which the oxide is dispersed in water or an organic solvent is preferable. The oxide dispersed in water is more preferable. When the oxide is dispersed in water, a dispersion stabilizer such as a polymer may be contained in order to disperse the oxide. The particle diameter of the oxide is preferably 1 to 500 nm, and more preferably 10 to 80 nm. When the catalyst containing the carrier is produced, a silica sol as a silica starting material is preferably added to the starting material slurry.

From the viewpoint of homogeneously dispersing the slurry, water-soluble polymers such as polyethylene glycol, methyl cellulose, polyvinyl alcohol, polyacrylic acid, and polyacrylamide, polyvalent carboxylic acids such as amines, aminocarboxylic acids, oxalic acid, malonic acid, and succinic acid, and organic acids such as glycolic acid, malic acid, tartaric acid, and citric acid can also be appropriately added into the starting material slurry. The amount of the organic acid added is not particularly limited. However, from the viewpoint of a balance between homogeneousity and the amount produced, the organic acid is preferably added in the range of 0 to 30% by mass based on the metal oxide.

The method for preparing the starting material slurry is not particularly limited as long as the method is a method which is usually used. For example, the starting material slurry can be prepared by mixing a solution in which an ammonium salt of molybdenum is dissolved in warm water with a solution obtained by using bismuth, cerium, iron, cobalt, or an alkali metal as a nitrate salt, and dissolving the nitrate salt in water or a nitric acid aqueous solution. From the viewpoint of the balance between the homogeneousity and the amount produced, the metal element concentration in the slurry after mixing is usually 1 to 50% by mass, preferably 10 to 40% by mass, and more preferably 20 to 40% by mass.

When the ammonium salt and the nitrate salt are mixed, a precipitate is produced, and is likely to form a slurry. However, the starting material slurry is preferably aged in a state where the starting material slurry is suspended. In the present specification, the "aging" of the slurry means that the slurry is held in the state where the slurry is suspended. It is preferable that the slurry is continuously and/or intermittently stirred in order to suspend the slurry. In this stirring step, the solid content is ground to promote the generation of a catalyst precursor, which can form a slurry which is finer and more homogeneous. When the content of Bi is increased, a slurry containing a large amount of nitric acid and having low dispersibility is apt to be formed, and therefore, aging is particularly preferably carried out.

When the slurry is aged, the slurry is desirably heated to a temperature which is higher than room temperature and at which a slurry medium remains liquid in order to obtain the desired complex crystal and/or the precursor thereof. Specifically, the temperature is preferably 20° C. to 90° C., more preferably 30° C. to 80° C., and still more preferably 50° C. to 70° C. General stirring means such as a stirring blade and a stirring bar can be used to stir the slurry. A stirring rate is different depending on the viscosity of the slurry or the like, and is preferably 50 to 3000 rpm. An aging time required for the generation of the catalyst precursor is different depending on the temperature and stirring energy of the slurry. As the temperature is higher or the stirring energy is larger, a suitable aging time tends to be shortened. For example, when the slurry temperature is 20° C. to 90° C., and a stirring treatment is carried out using a stirrer, the aging time is preferably 1 to 24 hours from the viewpoint of the productivity, more preferably 1 to 20 hours, and still more preferably 1 to 10 hours.

In the case of the slurry containing a large amount of solid content, the solid content in the slurry is preferably ground using a homogenizer or the like prior to the aging. When the slurry has a composition having an increased content of Bi as described above, the content of the nitric acid in the slurry tends to be also increased, and the dispersibility is apt to be decreased. Therefore, a homogenizer treatment is particularly effective. From the viewpoint of further finely grinding the solid content, the number of rotations of the homogenizer is preferably 5000 to 30000 rpm, more preferably 10000 to 20000 rpm, and still more preferably 15000 to 20000 rpm. The time of the homogenizer treatment is different depending on the number of rotations or the amount of the solid content. It is preferable that the time is generally 5 minutes to 2 hours.

When the starting material slurry is not homogeneous, the catalyst composition after calcining is heterogeneous, and it is difficult for the homogeneously complexed crystal structure to be formed. Therefore, when the obtained oxide is not sufficiently complexed, the step of preparing the slurry is preferably optimized. The above-mentioned step of preparing the starting material slurry is an example, and is not limited. The addition procedure of the element sources may be changed; the concentration of the nitric acid may be adjusted; or ammonia water may be added into the slurry to modify the pH and viscosity of the slurry. It is important to form a homogeneous slurry in order to form more crystal structures of Ce—Bi—Fe—Mo—O. From this viewpoint, the pH of the starting material slurry is preferably 2.0 or less. The pH of the starting material slurry is more preferably 1.5 or less, and still more preferably 1.0 or less. When the pH of the starting material slurry is more than 2.0, a precipitate of a bismuth compound may be generated to hinder the generation of the crystal structure of Ce—Bi—Fe—Mo—O.

(2) Drying

In the second step, the starting material slurry obtained in the first step is dried, to obtain dried particles. A drying method is not particularly limited, and drying can be carried out by a method which is generally used. The drying method can be carried out by any method such as an evaporation drying method, a spray dry method, and a reduced-pressure drying method. The spray dry method can be carried out by a method such as a centrifugal type, two-fluid nozzle type, and high-pressure nozzle type method which is usually carried out industrially. Air heated by steam and an electric heater or the like is preferably used as a drying heat source. In this case, the temperature of a dryer inlet of a spray dryer is usually 150 to 400° C., preferably 180 to 400° C., and more preferably 200 to 350° C.

(3) Calcination

In the third step, the dried particles obtained in the second step are calcined. The calcination can be carried out using a calcining furnace such as a rotary furnace, a tunnel furnace, and a muffle furnace. The dried particles are preferably calcined in two stages of preliminary calcination and final calcination. At the first stage, the preliminary calcination is usually carried out in the temperature range of 120 to 350° C., preferably 150° C. to 350° C., and more preferably 200° C. to 350° C. It is an object of the preliminary calcination to remove nitric acid remaining in the dried particles and to gradually burn an ammonium nitrate and contained organic substances derived from the starting material which is the ammonium salt and the starting material which is the nitrate salt. Therefore, the dried particles may be heated to the extent where the object can be achieved at the first calcining stage. A preliminary calcination time is usually 0.1 to 72 hours, preferably 1 to 48 hours, and more preferably 3 to 24 hours. In the case of a low temperature of 150° C. or less, the preliminary calcination is preferably carried out for a long period of time. In the case of a high temperature of 330° C. or more, the preliminary calcination is preferably carried out for a short period of time of 2 hours or less. When the temperature of the preliminary calcination is too high, or the time is too long, the oxide is likely to grow only in the two-component system of cerium and molybdenum at the stage of the preliminary calcination, and as a result, it is difficult for the crystal structure of Ce—Bi—Fe—Mo—O to be generated in the final calcination to be described later. Therefore, the upper limits of a preliminary calcination temperature and time are preferably set to the extent where the oxide of the two-component system of cerium and molybdenum are not generated.

In the case of the preliminary calcination, a temperature rising rate is desirably slow also from the viewpoint of suppressing a rapid burning reaction. The oxide catalyst in the present embodiment is a multicomponent system. Therefore, for example, when metal nitrates are used as the starting materials, the decomposition temperatures of the metal nitrates are different from each other, and nitric acid moves during calcination, and thereby the catalyst composition after calcination is apt to be heterogeneous. Particularly, when the content of Bi is increased, the amount of bismuth nitrate hardly soluble in water is increased, which increases the amount of nitric acid used for dissolution. For this reason, in order to form a structure which is more homogeneously complexed, it is preferable that the temperature is slowly risen to remove burning and decomposition components such as nitric acid and an organic substance. The temperature rising rate is usually 0.1° C./min to 100° C./min, more preferably 0.1° C./min to 75° C. min, and still more preferably 0.1° C./min to 50° C./min.

After the preliminary calcination, the final calcination as the second stage is preferably carried out. However, it is the object to facilitate the formation of a desired crystal structure. Because the crystal structure is influenced by the product of a calcination temperature and a calcination time according to the present inventors' findings, it is preferable that the calcination temperature and the calcination time are appropriately set. The temperature of the final calcination is preferably set to be higher than that of the preliminary calcination and 700° C. or less from the viewpoint of generating the crystal of Ce—Bi—Fe—Mo—O. From the viewpoint of the ease of the generation of the crystal structure of Ce—Bi—Fe—Mo—O, the calcination temperature of the final calcination is preferably 400 to 700° C., more preferably 400° C. to 650° C., and still more preferably 450° C. to 600° C. From the viewpoint of optimizing the product of the calcination temperature and the calcination time to promote the generation of the crystal when the calcination is carried out at such a temperature, the time of the final calcination is usually 0.1 to 72 hours, preferably 2 to 48 hours, and more preferably 3 to 24 hours. From the viewpoint of optimizing the calcination temperature×the calcination time in order to generate the crystal structure, in the case of a low temperature of 400° C. or less, for example, the final calcination is preferably carried out for a long period of time of about 24 to 72 hours. In the case of a high temperature of 600° C. or more, from the viewpoint of preventing the decrease of the activity of the catalyst caused by the excessive decrease of the surface area, the final calcination is preferably carried out for a short period of time of 1 hour or less.

The crystal structure of the complexed four-component system Ce—Bi—Fe—Mo—O is likely to be formed by carrying out all the above steps.

The generation of the crystal structure of the four-component system Ce—Bi—Fe—Mo—O in the final calcination step can be confirmed by carrying out X-ray structural analysis after the final calcination. If the crystal structure of the four-component system Ce—Bi—Fe—Mo—O is generated when the X-ray structural analysis is carried out after the final calcination, a peak is observed at 33.50°+α°. When the crystal of the oxide containing only cerium and molybdenum is generated, a peak appears at 33.50°. However, the peak shifts in the case of the four-component system Ce—Bi—Fe—Mo—O, and therefore, the generation of the crystal of the four-component system can be confirmed by using the shift as an index.

The magnitude of the shift (α°) is investigated, and the spacing d of the complex oxide of cerium and molybdenum showing a peak at 33.50° is taken as a reference. The change rate of d is investigated using the following formulae:

$$2d \sin \theta = n\lambda \text{ (}n\text{: integer)} \tag{II}$$

$$d \text{ change rate [ppm]} = (d^0 - d')/d^0 \times 1000000 \tag{III}$$

If the change rate of d is 5000 to 9000 ppm in the present embodiment, the crystal structure of the four-component system Ce—Bi—Fe—Mo—O is considered to be generated.

[3] Method for Producing Unsaturated Aldehyde

The unsaturated aldehyde can be produced by using the oxide catalyst according to the present embodiment and oxidizing at least one olefin selected from the group consisting of propylene and isobutylene and/or t-butyl alcohol. Hereinafter, the specific example thereof will be described. However, a production method according to the present embodiment is not limited to the following specific example.

(1) Method for Producing Methacrolein

Methacrolein can be obtained, for example, by subjecting isobutylene or t-butyl alcohol to a gas-phase catalytic oxidation reaction using the oxide catalyst according to the present embodiment. In the gas-phase catalytic oxidation reaction, a starting material gas containing a mixed gas to which a molecular oxygen-containing gas and a diluent gas are added is introduced into a catalyst layer in a fixed-bed reactor so that the concentration of molecular oxygen to isobutylene, t-butyl alcohol, or a mixed gas thereof of 1 to 10% by volume is 1 to 20% by volume. The concentration of isobutylene or t-butyl alcohol is usually 1 to 10% by volume, preferably 6 to 10% by volume, and more preferably 7 to 9% by volume. A reaction temperature is 300 to 480° C., preferably 350° C. to 450° C., and more preferably 400° C. to 450° C. A pressure is normal pressure to 5 atm, and the starting material gas can be introduced at a space velocity of 400 to 4000/hr [under a condition of normal temperature pressure (NTP)]. From the viewpoint of controlling the outlet oxygen concentration of the reactor in order to improve the yield of the unsaturated aldehyde, the molar ratio of oxygen and isobutylene or t-butyl alcohol, or a mixed gas thereof is usually 1.0 to 2.0, preferably 1.1 to 1.8, and more preferably 1.2 to 1.8.

Examples of the molecular oxygen-containing gas may include oxygen-containing gases such as pure oxygen gas, $N_2O$, or air. From the industrial viewpoint, the air is preferable. Examples of the diluent gas may include nitrogen, carbon dioxide, water vapor, and a mixed gas thereof. As for the mixing ratio of the molecular oxygen-containing gas and the diluent gas in the mixed gas, a condition of 0.01<molecular oxygen/molecular oxygen-containing gas+diluent gas)<0.3 is preferably satisfied in a volume ratio. Furthermore, the concentration of the molecular oxygen in the starting material gas is preferably 1 to 20% by volume.

The water vapor in the starting material gas is required from the viewpoint of preventing coking to the catalyst. However, the concentration of the water vapor in the diluent gas is preferably decreased as much as possible in order to suppress the subgeneration of a carboxylic acid such as methacrylic acid and acetic acid. The water vapor in the starting material gas is usually used in the range of 0 to 30% by volume.

(2) Method for Producing Acrolein

A condition or the like when acrolein is produced by the gas-phase catalytic oxidation of propylene is not particularly limited. The acrolein can be produced by a method generally used when acrolein is produced by the gas-phase catalytic oxidation of propylene. For example, a mixed gas containing 1 to 15% by volume of propylene, 3 to 30% by volume of molecular oxygen, 0 to 60% by volume of water vapor, and 20 to 80% by volume of an inert gas such as a nitrogen and carbon dioxide gas, or the like may be introduced into the catalyst layer in the reactor at 250 to 450° C., a pressure of 0.1 to 1 MPa, and a space velocity (SV) of 300 to 5000 hr$^{-1}$. A general fixed-bed reactor, fluid bed reactor, or moving bed reactor is used as the reactor.

EXAMPLES

Hereinafter, the present embodiment will be further described in detail with reference to Examples. However, the present embodiment is not limited to Examples described later. The atomic ratio of oxygen atoms in an oxide catalyst is determined depending on the valence conditions of the other elements. Therefore, in Examples and Comparative Examples, the atomic ratio of oxygen atoms is omitted in the formula representing a catalyst composition. The composition ratios of the elements in the oxide catalyst were calculated from the charging composition ratio.

<Measurement of X-Ray Diffraction Angle>

In measurement of XRD, a (111) plane and a (200) plane of a $LaB_6$ compound defined as a standard reference substance 660 by National Institute of Standards & Technology were measured. The values were normalized to 37.441 and 43.506°, respectively.

D8 ADVANCE manufactured by Bruker Corporation was used as an XRD apparatus. As XRD measurement conditions, X ray output: 40 kV-40 mA, a divergent slit (DS): 0.3°, a step width: 0.02°/step, a counting time: 2.0 sec, and a measurement range: 2θ=5° to 60° were set.

In Examples and Comparative Examples, a conversion rate, a selectivity, and a yield used in order to show reaction results are defined by the following formulae.

conversion rate=(number of moles of reacted starting material/number of moles of supplied starting material)×100 selectivity=(number of moles of compound generated/number of moles of reacted starting material)×100 yield=(number of moles of compound generated/number of moles of supplied starting material)×100

The productivity of a desired product is defined according to the following formula by calculating the amount of the desired product generated per 1 t of each of the catalysts, and thereafter assuming that a continuous operation is carried out using 10 t of the catalyst for 8000 hours.

productivity (t)=({number of moles (mol/h) of starting material supplied per hour×yield/amount (t) of catalyst}×10 (t)×8000 (hr)/molecular weight of desired product Example 1

65.7 g of ammonium heptamolybdate was dissolved in 197.0 g of warm water of about 90° C. (A liquid). 43.8 g of bismuth nitrate, 25.5 g of cerium nitrate, 36.4 g of iron nitrate, 0.66 g of cesium nitrate, and 34.5 g of cobalt nitrate were dissolved in 42.4 g of a nitric acid aqueous solution of 18% by mass, and 205.0 g of warm water of about 90° C. was added thereto (B liquid). Both the A liquid and the B liquid were mixed, and the mixture was treated at 20000 rpm for 1 hour using a homogenizer. Then, the treated mixture was aged by continuing stirring using a magnetic stirrer at about 65° C. for about 4 hours to obtain a starting material slurry. The starting material slurry was fed to a spray dryer, and spray-dried at an inlet temperature of 250° C. and an outlet temperature of about 140° C. The temperature of the obtained spray-dried catalyst precursor was further risen at a temperature rising rate of 1.4° C./min from room temperature, and the catalyst precursor was preliminarily calcined at 250° C. for 3 hours. The obtained preliminarily calcined catalyst precursor was finally calcined at 530° C. for 8 hours. The composition of the obtained oxide catalyst is shown in Table 1, and the measurement results of powder X-ray diffraction are shown in Table 2.

As the reaction evaluation of the catalyst, a SUS reaction tube with a jacket having a diameter of 14 mm was filled with 4.0 g of the catalyst. A mixed gas containing 8% by volume of isobutylene, 12.8% by volume of oxygen, 3.0% by volume of water vapor, and 76.2% by volume of nitrogen was aerated in a flow rate of 120 mL/min (NTP) at a reaction temperature of 430° C., to carry out a methacrolein synthetic reaction. The reaction evaluation results are shown in Table 3.

Example 2

Figure 2:
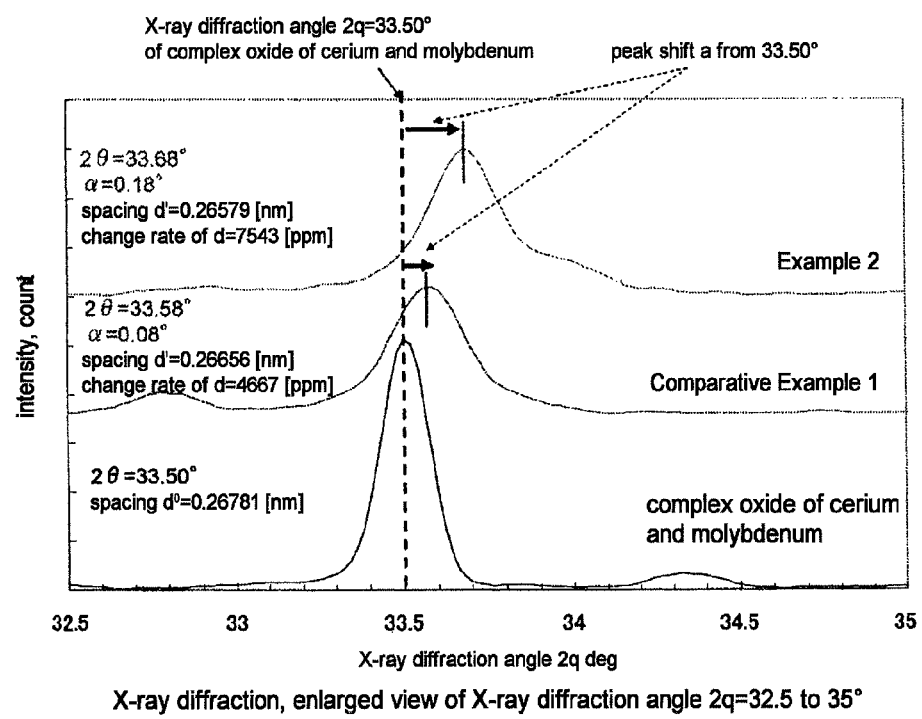
FIG. 2 shows an enlarged view of a range of 2θ=32.5 to 350 of the X-ray diffraction peaks in FIG. 1.

68.8 g of ammonium heptamolybdate was dissolved in 206.3 g of warm water of about 90° C. (A liquid). 33.2 g of bismuth nitrate, 29.6 g of cerium nitrate, 44.7 g of iron nitrate, 0.57 g of cesium nitrate, and 32.3 g of cobalt nitrate were dissolved in 42.6 g of a nitric acid aqueous solution of 18% by mass, and 196.2 g of warm water of about 90° C. was added thereto (B liquid). Both the A liquid and the B liquid were mixed, and the mixture was treated at 20000 rpm for 1 hour using a homogenizer. Then, the slurry was aged by stirring and mixing at about 65° C. for about 4 hours to obtain a starting material slurry. The starting material slurry was fed to a spray dryer, and spray-dried at an inlet temperature of 250° C. and an outlet temperature of about 140° C. The temperature of the obtained spray-dried catalyst precursor was further risen at a temperature rising rate of 1.4° C./min from room temperature, and the catalyst precursor was preliminarily calcined at 250° C. for 3 hours. The obtained preliminarily calcined catalyst precursor was finally calcined at 520° C. for 14 hours. The composition of the obtained oxide catalyst is shown in Table 1, and the measurement results of powder X-ray diffraction are shown in Table 2. X-ray diffraction patterns are shown in FIGS. 1 and 2. STEM-EDX analysis of a Bi-rich phase of the catalyst was carried out. As a result, if the atomic ratio of Bi was defined as 1, the atomic ratio of Ce was 0.32; the atomic ratio of Fe was 0.16; and the atomic ratio of Mo was 1.1. Ce, Fe, and Mo existed in a region in which a large number of Bi existed, and a crystal structure of the four-component system Ce—Bi—Fe—Mo—O was generated.

As the reaction evaluation of the catalyst, a reaction tube was filled with 3.5 g of the catalyst, and a methacrolein synthetic reaction was carried out under the same reaction condition as that of Example 1. The reaction evaluation results are shown in Table 3.

Example 3

67.4 g of ammonium heptamolybdate was dissolved in 202.3 g of warm water of about 90° C. (A liquid). 40.3 g of bismuth nitrate, 23.5 g of cerium nitrate, 50.3 g of iron nitrate, 0.56 g of cesium nitrate, and 28.0 g of cobalt nitrate were dissolved in 42.7 g of a nitric acid aqueous solution of 18% by mass, and 201.5 g of warm water of about 90° C. was added thereto (B liquid). Both the A liquid and the B liquid were mixed, and the mixture was treated at 20000 rpm for 1 hour using a homogenizer. Then, the slurry was aged by stirring and mixing at about 65° C. for about 4 hours to obtain a starting material slurry. The starting material slurry was fed to a spray dryer, and spray-dried at an inlet temperature of 250° C. and an outlet temperature of about 140° C. The temperature of the obtained spray-dried catalyst precursor was further risen at a temperature rising rate of 1.4° C./min from room temperature, and the catalyst precursor was preliminarily calcined at 250° C. for 3 hours. The obtained preliminarily calcined catalyst precursor was finally calcined at 540° C. for 3 hours. The composition of the obtained oxide catalyst is shown in Table 1, and the measurement results of powder X-ray diffraction are shown in Table 2.

As the reaction evaluation of the catalyst, a reaction tube was filled with 3.5 g of the catalyst, and a methacrolein synthetic reaction was carried out under the same reaction condition as that of Example 1. The reaction evaluation results are shown in Table 3.

Example 4

67.4 g of ammonium heptamolybdate was dissolved in 202.2 g of warm water of about 90° C. (A liquid). 40.3 g of bismuth nitrate, 23.5 g of cerium nitrate, 55.4 g of iron nitrate, 0.56 g of cesium nitrate, and 24.2 g of cobalt nitrate were dissolved in 42.9 g of a nitric acid aqueous solution of 18% by mass, and 202.7 g of warm water of about 90° C. was added thereto (B liquid). Both the A liquid and the B liquid were mixed, and the mixture was treated at 20000 rpm for 1 hour using a homogenizer. Then, the slurry was aged by stirring and mixing at about 65° C. for about 4 hours to obtain a starting material slurry. The starting material slurry was fed to a spray dryer, and spray-dried at an inlet temperature of 250° C. and an outlet temperature of about 140° C. The temperature of the obtained spray-dried catalyst precursor was further risen at a temperature rising rate of 1.4° C./min from room temperature, and the catalyst precursor was preliminarily calcined at 250° C. for 3 hours. The obtained preliminarily calcined catalyst precursor was finally canclined at 530° C. for 8 hours. The composition of the obtained oxide catalyst is shown in Table 1, and the measurement results of powder X-ray diffraction are shown in Table 2.

As the reaction evaluation of the catalyst, a reaction tube was filled with 3.5 g of the catalyst, and a methacrolein synthetic reaction was carried out under the same reaction condition as that of Example 1. The reaction evaluation results are shown in Table 3.

Example 5

67.2 g of ammonium heptamolybdate was dissolved in 201.6 g of warm water of about 90° C. (A liquid). 40.2 g of bismuth nitrate, 23.4 g of cerium nitrate, 60.4 g of iron nitrate, 0.55 g of cesium nitrate, 18.6 g of cobalt nitrate and 1.0 g of lead nitrate were dissolved in 37.9 g of a nitric acid aqueous solution of 18% by mass, and 203.9 g of warm water of about 90° C. was added thereto (B liquid). Both the A liquid and the B liquid were mixed, and the mixture was treated at 20000 rpm for 1 hour using a homogenizer. Then, the slurry was aged by stirring and mixing at about 65° C. for about 4 hours to obtain a starting material slurry. The starting material slurry was fed to a spray dryer, and spray-dried at an inlet temperature of 250° C. and an outlet temperature of about 140° C. The temperature of the obtained spray-dried catalyst precursor was further risen at a temperature rising rate of 1.4° C./min from room temperature, and the catalyst precursor was preliminarily calcined at 250° C. for 3 hours. The obtained preliminarily calcined catalyst precursor was finally calcined at 540° C. for 5 hours. The composition of the obtained oxide catalyst is shown in Table 1, and the measurement results of powder X-ray diffraction are shown in Table 2.

As the reaction evaluation of the catalyst, a reaction tube was filled with 3.6 g of the catalyst, and a methacrolein synthetic reaction was carried out under the same reaction condition as that of Example 1. The reaction evaluation results are shown in Table 3.

Example 6

66.2 g of ammonium heptamolybdate was dissolved in 198.56 g of warm water of about 90° C. (A liquid). 39.6 g of bismuth nitrate, 23.0 g of cerium nitrate, 59.5 g of iron nitrate, 0.36 g of cesium nitrate, 18.3 g of cobalt nitrate and 9.1 g of nickel nitrate were dissolved in 38.4 g of a nitric acid aqueous solution of 18% by mass, and 210.0 g of warm water of about 90° C. was added thereto (B liquid). Both the A liquid and the B liquid were mixed, and the mixture was treated at 20000 rpm for 1 hour using a homogenizer. Then, the slurry was aged by stirring and mixing at about 65° C. for about 4 hours to obtain a starting material slurry. The starting material slurry was fed to a spray dryer, and spray-dried at an inlet temperature of 250° C. and an outlet temperature of about 140° C. The temperature of the obtained spray-dried catalyst precursor was further risen at a temperature rising rate of 1.4° C./min from room temperature, and the catalyst precursor was preliminarily calcined at 250° C. for 3 hours. The obtained preliminarily calcined catalyst precursor was finally calcined at 520° C. for 14 hours. The composition of the obtained oxide catalyst is shown in Table 1, and the measurement results of powder X-ray diffraction are shown in Table 2.

As the reaction evaluation of the catalyst, a reaction tube was filled with 3.0 g of the catalyst, and a methacrolein synthetic reaction was carried out under the same reaction condition as that of Example 1. The reaction evaluation results are shown in Table 3.

Example 7

67.4 g of ammonium heptamolybdate was dissolved in 202.1 g of warm water of about 90° C. (A liquid). 40.3 g of bismuth nitrate, 23.4 g of cerium nitrate, 55.4 g of iron nitrate, 0.56 g of cesium nitrate, 22.3 g of cobalt nitrate and 1.5 g of copper nitrate were dissolved in 37.9 g of a nitric acid aqueous solution of 18% by mass, and 203.1 g of warm water of about 90° C. was added thereto (B liquid). Both the A liquid and the B liquid were mixed, and the mixture was treated at 20000 rpm for 1 hour using a homogenizer. Then, the slurry was aged by stirring and mixing at about 65° C. for about 4 hours to obtain a starting material slurry. The starting material slurry was fed to a spray dryer, and spray-dried at an inlet temperature of 250° C. and an outlet temperature of about 140° C. The temperature of the obtained spray-dried catalyst precursor was further risen at a temperature rising rate of 1.4° C./min from room temperature, and the catalyst precursor was preliminarily calcined at 250° C. for 3 hours. The obtained preliminarily calcined catalyst precursor was finally calcined at 550° C. for 3 hours. The composition of the obtained oxide catalyst is shown in Table 1, and the measurement results of powder X-ray diffraction are shown in Table 2.

As the reaction evaluation of the catalyst, a reaction tube was filled with 3.2 g of the catalyst, and a methacrolein synthetic reaction was carried out under the same reaction condition as that of Example 1. The reaction evaluation results are shown in Table 3.

Example 8

67.0 g of ammonium heptamolybdate was dissolved in 202.1 g of warm water of about 90° C. (A liquid). 44.7 g of bismuth nitrate, 26.1 g of cerium nitrate, 37.2 g of iron nitrate, 0.51 g of rubidium nitrate, 18.5 g of cobalt nitrate and 14.6 g of magnesium nitrate were dissolved in 37.7 g of a nitric acid aqueous solution of 18% by mass, and 203.1 g of warm water of about 90° C. was added thereto (B liquid). Both the A liquid and the B liquid were mixed, and the mixture was treated at 20000 rpm for 1 hour using a homogenizer. Then, the slurry was aged by stirring and mixing at about 65° C. for about 4 hours to obtain a starting material slurry. The starting material slurry was fed to a spray dryer, and spray-dried at an inlet temperature of 250° C. and an outlet temperature of about 140° C. The temperature of the obtained spray-dried catalyst precursor was further risen at a temperature rising rate of 1.4° C./min from room temperature, and the catalyst precursor was preliminarily calcined at 250° C. for 3 hours. The obtained preliminarily calcined catalyst precursor was finally calcined at 540° C. for 3 hours. The composition of the obtained oxide catalyst is shown in Table 1, and the measurement results of powder X-ray diffraction are shown in Table 2.

As the reaction evaluation of the catalyst, a reaction tube was filled with 3.1 g of the catalyst, and a methacrolein synthetic reaction was carried out under the same reaction condition as that of Example 1. The reaction evaluation results are shown in Table 3.

Example 9

67.4 g of ammonium heptamolybdate was dissolved in 202.2 g of warm water of about 90° C. (A liquid). 40.3 g of bismuth nitrate, 23.5 g of cerium nitrate, 55.4 g of iron nitrate, 0.56 g of cesium nitrate, and 24.2 g of cobalt nitrate were dissolved in 42.9 g of a nitric acid aqueous solution of 18% by mass, and 202.7 g of warm water of about 90° C. was added thereto (B liquid). Both the A liquid and the B liquid were mixed, and the mixture was treated at 20000 rpm for 1 hour using a homogenizer. Then, the slurry was aged by stirring and mixing at about 65° C. for about 4 hours to obtain a starting material slurry. The starting material slurry was fed to a spray dryer, and spray-dried at an inlet temperature of 250° C. and an outlet temperature of about 140° C. The temperature of the obtained spray-dried catalyst precursor was further risen at a temperature rising rate of 1.4° C./min from room temperature, and the catalyst precursor was preliminarily calcined at 150° C. for 36 hours. The obtained preliminarily calcined catalyst precursor was finally calcined at 520° C. for 8 hours. The composition of the obtained oxide catalyst is shown in Table 1, and the measurement results of powder X-ray diffraction are shown in Table 2.

As the reaction evaluation of the catalyst, a reaction tube was filled with 3.9 g of the catalyst, and a methacrolein synthetic reaction was carried out under the same reaction condition as that of Example 1. The reaction evaluation results are shown in Table 3.

Example 10

67.4 g of ammonium heptamolybdate was dissolved in 202.2 g of warm water of about 90° C. (A liquid). 40.3 g of bismuth nitrate, 23.5 g of cerium nitrate, 55.4 g of iron nitrate, 0.56 g of cesium nitrate, and 24.2 g of cobalt nitrate were dissolved in 42.9 g of a nitric acid aqueous solution of 18% by mass, and 202.7 g of warm water of about 90° C. was added thereto (B liquid). Both the A liquid and the B liquid were mixed, and the mixture was treated at 20000 rpm for 1 hour using a homogenizer. Then, the slurry was aged by stirring and mixing at about 65° C. for about 4 hours to obtain a starting material slurry. The starting material slurry was fed to a spray dryer, and spray-dried at an inlet temperature of 250° C. and an outlet temperature of about 140° C. The temperature of the obtained spray-dried catalyst precursor was further risen at a temperature rising rate of 75° C./min from room temperature, and the catalyst precursor was preliminarily calcined at 250° C. for 3 hours. The obtained preliminarily calcined catalyst precursor was finally calcined at 530° C. for 4 hours. The composition of the obtained oxide catalyst is shown in Table 1, and the measurement results of powder X-ray diffraction are shown in Table 2.

As the reaction evaluation of the catalyst, a reaction tube was filled with 3.9 g of the catalyst, and a methacrolein synthetic reaction was carried out under the same reaction condition as that of Example 1. The reaction evaluation results are shown in Table 3.

Example 11

67.4 g of ammonium heptamolybdate was dissolved in 202.2 g of warm water of about 90° C. (A liquid). 40.3 g of bismuth nitrate, 23.5 g of cerium nitrate, 55.4 g of iron nitrate, 0.56 g of cesium nitrate, and 24.2 g of cobalt nitrate were dissolved in 42.9 g of a nitric acid aqueous solution of 18% by mass, and 202.7 g of warm water of about 90° C. was added thereto (B liquid). Both the A liquid and the B liquid were mixed, and the mixture was treated at 20000 rpm for 1 hour using a homogenizer. Then, the slurry was aged by stirring and mixing at about 65° C. for about 4 hours to obtain a starting material slurry. The starting material slurry was fed to a spray dryer, and spray-dried at an inlet temperature of 250° C. and an outlet temperature of about 140° C. The temperature of the obtained spray-dried catalyst precursor was further risen at a temperature rising rate of 1.4° C./min from room temperature, and the catalyst precursor was preliminarily calcined at 250° C. for 3 hours. The obtained preliminarily calcined catalyst precursor was finally calcined at 400° C. for 48 hours. The composition of the obtained oxide catalyst is shown in Table 1, and the measurement results of powder X-ray diffraction are shown in Table 2.

As the reaction evaluation of the catalyst, a reaction tube was filled with 3.2 g of the catalyst, and a methacrolein synthetic reaction was carried out under the same reaction condition as that of Example 1. The reaction evaluation results are shown in Table 3.

Example 12

67.4 g of ammonium heptamolybdate was dissolved in 202.2 g of warm water of about 90° C. (A liquid). 40.3 g of bismuth nitrate, 23.5 g of cerium nitrate, 55.4 g of iron nitrate, 0.56 g of cesium nitrate, and 24.2 g of cobalt nitrate were dissolved in 42.9 g of a nitric acid aqueous solution of 18% by mass, and 202.7 g of warm water of about 90° C. was added thereto (B liquid). Both the A liquid and the B liquid were mixed, and the mixture was treated at 20000 rpm for 1 hour using a homogenizer. Then, the slurry was aged by stirring and mixing at about 65° C. for about 4 hours to obtain a starting material slurry. The starting material slurry was fed to a spray dryer, and spray-dried at an inlet temperature of 250° C. and an outlet temperature of about 140° C. The temperature of the obtained spray-dried catalyst precursor was further risen at a temperature rising rate of 1.4° C./min from room temperature, and the catalyst precursor was preliminarily calcined at 250° C. for 3 hours. The obtained preliminarily calcined catalyst precursor was finally calcined at 640° C. for 30 minutes. The composition of the obtained oxide catalyst is shown in Table 1, and the measurement results of powder X-ray diffraction are shown in Table 2.

As the reaction evaluation of the catalyst, a reaction tube was filled with 5.4 g of the catalyst, and a methacrolein synthetic reaction was carried out under the same reaction condition as that of Example 1. The reaction evaluation results are shown in Table 3.

Example 13

The same catalyst as that of Example 3 was used. As the reaction evaluation of the catalyst, a reaction tube was filled with 6.4 g of the catalyst. A methacrolein synthetic reaction was carried out under the same reaction condition as that of Example 1 except that the reaction temperature was changed to 400° C. The reaction evaluation results are shown in Table 3.

Example 14

The same catalyst as that of Example 3 was used. As the reaction evaluation of the catalyst, a reaction tube was filled with 3.0 g of the catalyst. A methacrolein synthetic reaction was carried out under the same reaction condition as that of Example 1 except that the reaction temperature was changed to 460° C. The reaction evaluation results are shown in Table 3.

Example 15

69.5 g of ammonium heptamolybdate was dissolved in 208.5 g of warm water of about 90° C. (A liquid). 32.0 g of bismuth nitrate, 7.2 g of cerium nitrate, 39.9 g of iron nitrate, 1.3 g of cesium nitrate, 43.2 g of cobalt nitrate and 24.2 g of nickel nitrate were dissolved in 38.3 g of a nitric acid aqueous solution of 18% by mass, and 208.5 g of warm water of about 90° C. was added thereto (B liquid). Both the A liquid and the B liquid were mixed, and the mixture was treated at 20000 rpm for 1 hour using a homogenizer. Then, the treated mixture was aged by stirring and mixing at about 60° C. for about 4 hours to obtain a starting material slurry. The starting material slurry was fed to a spray dryer, and spray-dried at an inlet temperature of 250° C. and an outlet temperature of about 140° C. The temperature of the obtained spray-dried catalyst precursor was further risen at a temperature rising rate of 1.4° C./min from room temperature, and the catalyst precursor was preliminarily calcined at 280° C. for 3 hours. The obtained preliminarily calcined catalyst precursor was finally calcined at 550° C. for 10 hours. The composition of the obtained oxide catalyst is shown in Table 1, and the measurement results of powder X-ray diffraction are shown in Table 2.

As the reaction evaluation of the catalyst, a reaction tube was filled with 4.0 g of the catalyst, and a methacrolein synthetic reaction was carried out under the same reaction condition as that of Example 1. The reaction evaluation results are shown in Table 3.

Example 16

Both the A liquid and the B liquid are mixed in the same composition as that of Example 1, and the mixture was aged by continuing stirring using a magnetic stirrer at about 65° C. for about 1 hour without carrying out a homogenizer treatment to obtain a starting material slurry. The starting material slurry was fed to a spray dryer, and spray-dried at an inlet temperature of 250° C. and an outlet temperature of about 140° C. The temperature of the obtained spray-dried catalyst precursor was further risen at a temperature rising rate of 1.4° C./min from room temperature, and the catalyst precursor was preliminarily calcined at 250° C. for 3 hours. The obtained preliminarily calcined catalyst precursor was finally calcined at 530° C. for 8 hours. The composition of the obtained oxide catalyst is shown in Table 1, and the measurement results of powder X-ray diffraction are shown in Table 2.

As the reaction evaluation of the catalyst, a reaction tube was filled with 4.0 g of the catalyst, and a methacrolein synthetic reaction was carried out under the same reaction condition as that of Example 1. The reaction evaluation results are shown in Table 3.

Example 17

Both the A liquid and the B liquid are mixed in the same composition as that of Example 1, and the mixture was aged by continuing stirring using a magnetic stirrer at about 65° C. for about 24 hours without carrying out a homogenizer treatment to obtain a starting material slurry. The starting material slurry was fed to a spray dryer, and spray-dried at an inlet temperature of 250° C. and an outlet temperature of about 140° C. The temperature of the obtained spray-dried catalyst precursor was further risen at a temperature rising rate of 1.4° C./min from room temperature, and the catalyst precursor was preliminarily calcined at 250° C. for 3 hours. The obtained preliminarily calcined catalyst precursor was finally calcined at 530° C. for 8 hours. The composition of the obtained oxide catalyst is shown in Table 1, and the measurement results of powder X-ray diffraction are shown in Table 2.

As the reaction evaluation of the catalyst, a reaction tube was filled with 4.0 g of the catalyst, and a methacrolein synthetic reaction was carried out under the same reaction condition as that of Example 1. The reaction evaluation results are shown in Table 3.

Example 18

The same catalyst as that of Example 1 was used, and as the reaction evaluation of the catalyst, a reaction tube was filled with 4.5 g of the catalyst. A methacrolein synthetic reaction was carried out under the same reaction condition as that of Example 1 except that a reaction temperature was set to 350° C. The reaction evaluation results are shown in Table 3.

Example 19

The same catalyst as that of Example 1 was used, and as the reaction evaluation of the catalyst, a reaction tube was filled with 4.0 g of the catalyst. A methacrolein synthetic reaction was carried out under the same reaction condition as that of Example 1 except that a reaction temperature was set to 480° C. The reaction evaluation results are shown in Table 3.

Example 20

The same catalyst as that of Example 1 was used, and as the reaction evaluation of the catalyst, a reaction tube was filled with 4.0 g of the catalyst. A mixed gas containing 6% by volume of isobutylene, 9.6% by volume of oxygen, 3.0% by volume of water vapor, and 81.4% by volume of nitrogen was aerated in a flow rate of 100 mL/min (NTP) at a reaction temperature of 430° C., to carry out a methacrolein synthetic reaction. The reaction evaluation results are shown in Table 3.

Example 21

The same catalyst as that of Example 1 was used, and as the reaction evaluation of the catalyst, a reaction tube was filled with 4.0 g of the catalyst. A methacrolein synthetic reaction was carried out under the same reaction condition as that of Example 20 except that a reaction temperature was set to 350° C. The reaction evaluation results are shown in Table 3.

Comparative Example 1

72.8 g of ammonium heptamolybdate was dissolved in 218.4 g of warm water of about 90° C. (A liquid). 26.8 g of bismuth nitrate, 7.5 g of cerium nitrate, 19.5 g of iron nitrate, 2.0 g of cesium nitrate, and 79.5 g of cobalt nitrate were dissolved in 42.1 g of a nitric acid aqueous solution of 18% by mass, and 177.8 g of warm water of about 90° C. was added thereto (B liquid). Both the A liquid and the B liquid were mixed, and the mixture was treated at 20000 rpm for 1 hour using a homogenizer. Then, the treated mixture was aged by stirring and mixing at about 65° C. for about 4 hours to obtain a starting material slurry. The starting material slurry was fed to a spray dryer, and spray-dried at an inlet temperature of 250° C. and an outlet temperature of about 140° C. The temperature of the obtained spray-dried catalyst precursor was further risen at a temperature rising rate of 1.4° C./min from room temperature, and the catalyst precursor was preliminarily calcined at 250° C. for 3 hours. The obtained preliminarily calcined catalyst precursor was finally calcined at 520° C. for 5 hours. The composition of the obtained oxide catalyst is shown in Table 1, and the measurement results of powder X-ray diffraction are shown in Table 2. X-ray diffraction patterns are shown in FIGS. 1 and 2.

STEM-EDX analysis of a Bi-rich phase of the catalyst was carried out. As a result, if the atomic ratio of Bi was defined as 1, the atomic ratio of Ce was 0.07; the atomic ratio of Fe was 0.06; and the atomic ratio of Mo was 1.1. The contents of Ce and Fe to Bi were less than those of Example 2, and the two-component system Bi—Mo—O was generated. The amount generated of the four-component crystal structure of Ce—Bi—Mo—O was less.

As the reaction evaluation of the catalyst, a reaction tube was filled with 4.2 g of the catalyst, and a methacrolein synthetic reaction was carried out under the same reaction condition as that of Example 1. The reaction evaluation results are shown in Table 3.

Comparative Example 2

66.0 g of ammonium heptamolybdate was dissolved in 197.9 g of warm water of about 90° C. (A liquid). 39.5 g of bismuth nitrate, 23.0 g of cerium nitrate, 75.7 g of iron nitrate, 0.54 g of cesium nitrate, and 15.5 g of cobalt nitrate were dissolved in 42.1 g of a nitric acid aqueous solution of 18% by mass, and 214.4 g of warm water of about 90° C. was added thereto (B liquid). Both the A liquid and the B liquid were mixed, and the mixture was treated at 20000 rpm for 1 hour using a homogenizer. Then, the treated mixture was aged by stirring and mixing at about 65° C. for about 4 hours to obtain a starting material slurry. The starting material slurry was fed to a spray dryer, and spray-dried at an inlet temperature of 250° C. and an outlet temperature of about 140° C. The temperature of the obtained spray-dried catalyst precursor was further risen at a temperature rising rate of 1.4° C./min from room temperature, and the catalyst precursor was preliminarily calcined at 250° C. for 3 hours. The obtained preliminarily calcined catalyst precursor was finally calcined at 540° C. for 5 hours. The composition of the obtained oxide catalyst is shown in Table 1, and the measurement results of powder X-ray diffraction are shown in Table 2.

As the reaction evaluation of the catalyst, a reaction tube was filled with 4.3 g of the catalyst, and a methacrolein synthetic reaction was carried out under the same reaction condition as that of Example 1. The reaction evaluation results are shown in Table 3.

Comparative Example 3

67.4 g of ammonium heptamolybdate was dissolved in 202.2 g of warm water of about 90° C. (A liquid). 40.3 g of bismuth nitrate, 23.5 g of cerium nitrate, 55.4 g of iron nitrate, 0.56 g of cesium nitrate, and 24.2 g of cobalt nitrate were dissolved in 42.9 g of a nitric acid aqueous solution of 18% by mass, and 202.7 g of warm water of about 90° C. was added thereto (B liquid). Both the A liquid and the B liquid were mixed to obtain a starting material slurry. The starting material slurry was fed to a spray dryer, and spray-dried at an inlet temperature of 250° C. and an outlet temperature of about 140° C. The temperature of the obtained spray-dried catalyst precursor was further risen at a temperature rising rate of 1.4° C./min from room temperature, and the catalyst precursor was preliminarily calcined at 250° C. for 3 hours. The obtained preliminarily calcined catalyst precursor was finally calcined at 540° C. for 5 hours. The composition of the obtained oxide catalyst is shown in Table 1, and the measurement results of powder X-ray diffraction are shown in Table 2.

As the reaction evaluation of the catalyst, a reaction tube was filled with 4.6 g of the catalyst, and a methacrolein synthetic reaction was carried out under the same reaction condition as that of Example 1. The reaction evaluation results are shown in Table 3.

Comparative Example 4

67.4 g of ammonium heptamolybdate was dissolved in 202.2 g of warm water of about 90° C. (A liquid). 40.3 g of bismuth nitrate, 23.5 g of cerium nitrate, 55.4 g of iron nitrate, 0.56 g of cesium nitrate, and 24.2 g of cobalt nitrate were dissolved in 42.9 g of a nitric acid aqueous solution of 18% by mass, and 202.7 g of warm water of about 90° C. was added thereto (B liquid). Both the A liquid and the B liquid were mixed, and the mixture was treated at 20000 rpm for 1 hour using a homogenizer. Then, the treated mixture was aged by stirring and mixing at about 65° C. for about 4 hours to obtain a starting material slurry. The starting material slurry was fed to a spray dryer, and spray-dried at an inlet temperature of 250° C. and an outlet temperature of about 140° C. The temperature of the obtained spray-dried catalyst precursor was further risen at a temperature rising rate of 1.4° C./min from room temperature, and the catalyst precursor was preliminarily calcined at 105° C. for 12 hours. The obtained preliminarily calcined catalyst precursor was finally calcined at 530° C. for 8 hours. The composition of the obtained oxide catalyst is shown in Table 1, and the measurement results of powder X-ray diffraction are shown in Table 2.

As the reaction evaluation of the catalyst, a reaction tube was filled with 4.9 g of the catalyst, and a methacrolein synthetic reaction was carried out under the same reaction condition as that of Example 1. The reaction evaluation results are shown in Table 3.

Comparative Example 5

67.4 g of ammonium heptamolybdate was dissolved in 202.2 g of warm water of about 90° C. (A liquid). 40.3 g of bismuth nitrate, 23.5 g of cerium nitrate, 55.4 g of iron nitrate, 0.56 g of cesium nitrate, and 24.2 g of cobalt nitrate were dissolved in 42.9 g of a nitric acid aqueous solution of 18% by mass, and 202.7 g of warm water of about 90° C. was added thereto (B liquid). Both the A liquid and the B liquid were mixed, and the mixture was treated at 20000 rpm for 1 hour using a homogenizer. Then, the treated mixture was aged by stirring and mixing at about 65° C. for about 4 hours to obtain a starting material slurry. The starting material slurry was fed to a spray dryer, and spray-dried at an inlet temperature of 250° C. and an outlet temperature of about 140° C. The temperature of the obtained spray-dried catalyst precursor was further risen at a temperature rising rate of 1.4° C./min from room temperature, and the catalyst precursor was preliminarily calcined at 250° C. for 3 hours. The obtained preliminarily calcined catalyst precursor was finally calcined at 720° C. for 30 minutes. The composition of the obtained oxide catalyst is shown in Table 1, and the measurement results of powder X-ray diffraction are shown in Table 2.

As the reaction evaluation of the catalyst, a reaction tube was filled with 5.9 g of the catalyst, and a methacrolein synthetic reaction was carried out under the same reaction condition as that of Example 1. The reaction evaluation results are shown in Table 3.

Comparative Example 6

A catalyst was prepared in the same manner as in Example 15 except that a starting material slurry was not aged. The composition of the obtained oxide catalyst is shown in Table 1, and the measurement results of powder X-ray diffraction are shown in Table 2.

As the reaction evaluation of the catalyst, a reaction tube was filled with 4.5 g of the catalyst, and a methacrolein synthetic reaction was carried out under the same reaction condition as that of Example 1. The reaction evaluation results are shown in Table 3.

Comparative Example 7

A catalyst was prepared in the same manner as in Example 1 except that a starting material slurry was not aged. The obtained catalyst was used, and as the reaction evaluation of the catalyst, a reaction tube was filled with 4.0 g of the catalyst. A methacrolein synthetic reaction was carried out under the same reaction condition as that of Example 1. The reaction evaluation results are shown in Table 3.

Comparative Example 8

A catalyst was prepared in the same manner as in Example 1 except that a starting material slurry was not aged. The obtained catalyst was used, and as the reaction evaluation of the catalyst, a reaction tube was filled with 5.0 g of the catalyst. A methacrolein synthetic reaction was carried out under the same reaction condition as that of Example 18. The reaction evaluation results are shown in Table 3.

Comparative Example 9

A catalyst was prepared in the same manner as in Example 1 except that a starting material slurry was not aged. The obtained catalyst was used, and as the reaction evaluation of the catalyst, a reaction tube was filled with 4.0 g of the catalyst. A methacrolein synthetic reaction was carried out under the same reaction condition as that of Example 19. The reaction evaluation results are shown in Table 3.

Comparative Example 10

A catalyst was prepared in the same manner as in Example 1 except that a starting material slurry was not aged. The obtained catalyst was used, and as the reaction evaluation of the catalyst, a reaction tube was filled with 5.0 g of the catalyst. A methacrolein synthetic reaction was carried out under the same reaction condition as that of Example 20. The reaction evaluation results are shown in Table 3.

Comparative Example 11

A catalyst was prepared in the same manner as in Example 1 except that a starting material slurry was not aged. The obtained catalyst was used, and as the reaction evaluation of the catalyst, a reaction tube was filled with 6.0 g of the catalyst. A methacrolein synthetic reaction was carried out under the same reaction condition as that of Example 21. The reaction evaluation results are shown in Table 3.

Comparative Example 12

71.2 g of ammonium heptamolybdate was dissolved in 213.7 g of warm water of about 90° C. (A liquid). 32.8 g of bismuth nitrate, 14.6 g of cerium nitrate, 34.1 g of iron nitrate, 2.6 g of cesium nitrate, 49.2 g of cobalt nitrate and 0.35 g of potassium nitrate were dissolved in 37.0 g of a nitric acid aqueous solution of 18% by mass, and 183.2 g of warm water of about 90° C. was added thereto (B liquid). Both the A liquid and the B liquid were mixed to obtain a starting material slurry. The starting material slurry was fed to a spray dryer, and spray-dried at an inlet temperature of 250° C. and an outlet temperature of about 140° C. The temperature of the obtained spray-dried catalyst precursor was further risen at a temperature rising rate of 1.4° C./min from room temperature, and the catalyst precursor was preliminarily calcined at 250° C. for 3 hours. The obtained preliminarily calcined catalyst precursor was finally calcined at 510° C. for 3 hours. The composition of the obtained oxide catalyst is shown in Table 1, and the measurement results of powder X-ray diffraction are shown in Table 2.

As the reaction evaluation of the catalyst, a reaction tube was filled with 3.8 g of the catalyst, and a methacrolein synthetic reaction was carried out under the same reaction condition as that of Example 1. The reaction evaluation results are shown in Table 3.

TABLE 1

| | Atomic composition | | | | | | | | |
|---|---|---|---|---|---|---|---|---|---|
| Number | Mo | Bi | Fe | Co | Ce A | B | Fe/(Co + B) ratio | Fe/Co ratio | Other elements |
| Example 1 | 12.0 | 2.9 | 2.9 | 3.8 | 1.9 Cs0.11 | 0 | 0.76 | 0.76 | |
| Example 2 | 12.0 | 2.1 | 3.4 | 3.4 | 2.1 Cs0.09 | 0 | 1.00 | 1.00 | |
| Example 3 | 12.0 | 2.6 | 3.9 | 3.0 | 1.7 Cs0.09 | 0 | 1.30 | 1.30 | |
| Example 4 | 12.0 | 2.6 | 4.3 | 2.6 | 1.7 Cs0.09 | 0 | 1.65 | 1.65 | |
| Example 5 | 12.0 | 2.6 | 4.7 | 2.0 | 1.7 Cs0.06 | Pb0.1 | 2.24 | 2.35 | |
| Example 6 | 12.0 | 2.6 | 4.7 | 2.0 | 1.7 Cs0.09 | Ni1.0 | 1.57 | 2.35 | |
| Example 7 | 12.0 | 2.6 | 4.3 | 2.4 | 1.7 Cs0.09 | Cu0.2 | 1.65 | 1.79 | |
| Example 8 | 12.0 | 2.9 | 2.9 | 2.0 | 1.9 Rb0.11 | Mg1.8 | 0.76 | 1.45 | |
| Example 9 | 12.0 | 2.6 | 4.3 | 2.6 | 1.7 Cs0.09 | 0 | 1.65 | 1.65 | |
| Example 10 | 12.0 | 2.6 | 4.3 | 2.6 | 1.7 Cs0.09 | 0 | 1.65 | 1.65 | |
| Example 11 | 12.0 | 2.6 | 4.3 | 2.6 | 1.7 Cs0.09 | 0 | 1.65 | 1.65 | |
| Example 12 | 12.0 | 2.6 | 4.3 | 2.6 | 1.7 Cs0.09 | 0 | 1.65 | 1.65 | |
| Example 13 | 12.0 | 2.6 | 3.9 | 3.0 | 1.7 Cs0.09 | 0 | 1.30 | 1.30 | |
| Example 14 | 12.0 | 2.6 | 3.9 | 3.0 | 1.7 Cs0.09 | 0 | 1.30 | 1.30 | |
| Example 15 | 12.0 | 2.0 | 3.0 | 4.5 | 0.5 Cs0.2 | Ni2.5 | 0.43 | 0.67 | |
| Example 16 | 12.0 | 2.9 | 2.9 | 3.8 | 1.9 Cs0.11 | 0 | 0.76 | 0.76 | |
| Example 17 | 12.0 | 2.9 | 2.9 | 3.8 | 1.9 Cs0.11 | 0 | 0.76 | 0.76 | |
| Example 18 | 12.0 | 2.9 | 2.9 | 3.8 | 1.9 Cs0.11 | 0 | 0.76 | 0.76 | |
| Example 19 | 12.0 | 2.9 | 2.9 | 3.8 | 1.9 Cs0.11 | 0 | 0.76 | 0.76 | |
| Example 20 | 12.0 | 2.9 | 2.9 | 3.8 | 1.9 Cs0.11 | 0 | 0.76 | 0.76 | |
| Example 21 | 12.0 | 2.9 | 2.9 | 3.8 | 1.9 Cs0.11 | 0 | 0.76 | 0.76 | |
| Comparative Example 1 | 12.0 | 1.6 | 1.4 | 7.9 | 0.5 Cs0.3 | 0 | 0.18 | 0.18 | |
| Comparative Example 2 | 12.0 | 2.6 | 6.0 | 1.7 | 1.7 Cs0.09 | 0 | 3.53 | 3.53 | |
| Comparative Example 3 | 12.0 | 2.6 | 4.3 | 2.6 | 1.7 Cs0.09 | 0 | 1.65 | 1.65 | |
| Comparative Example 4 | 12.0 | 2.6 | 4.3 | 2.6 | 1.7 Cs0.09 | 0 | 1.65 | 1.65 | |
| Comparative Example 5 | 12.0 | 2.6 | 4.3 | 2.6 | 1.7 Cs0.09 | 0 | 1.65 | 1.65 | |
| Comparative Example 6 | 12.0 | 2.0 | 3.0 | 4.5 | 0.5 Cs0.2 | Ni2.5 | 0.43 | 0.67 | |
| Comparative Example 7 | 12.0 | 2.9 | 2.9 | 3.8 | 1.9 Cs0.11 | 0 | 0.76 | 0.76 | |
| Comparative Example 8 | 12.0 | 2.9 | 2.9 | 3.8 | 1.9 Cs0.11 | 0 | 0.76 | 0.76 | |
| Comparative Example 9 | 12.0 | 2.9 | 2.9 | 3.8 | 1.9 Cs0.11 | 0 | 0.76 | 0.76 | |
| Comparative Example 10 | 12.0 | 2.9 | 2.9 | 3.8 | 1.9 Cs0.11 | 0 | 0.76 | 0.76 | |
| Comparative Example 11 | 12.0 | 2.9 | 2.9 | 3.8 | 1.9 Cs0.11 | 0 | 0.76 | 0.76 | |
| Comparative Example 12 | 12.0 | 2.0 | 2.5 | 5.0 | 1.0 Cs0.4 | 0 | 0.50 | 0.50 | K0.1 |

TABLE 2

| Number | X-ray diffraction angle 2θ (descending order of intensities) First | Second | Third | Change rate of spacing d, ppm |
|---|---|---|---|---|
| Example 1 | 28.17 | 33.64 | 26.42 | 6385 |
| Example 2 | 28.18 | 33.68 | 26.44 | 7543 |
| Example 3 | 28.12 | 33.68 | 26.42 | 7543 |
| Example 4 | 28.12 | 33.70 | 26.42 | 8103 |
| Example 5 | 28.14 | 33.70 | 26.42 | 8103 |
| Example 6 | 28.14 | 33.70 | 26.42 | 8103 |
| Example 7 | 28.12 | 33.70 | 26.42 | 8103 |
| Example 8 | 28.17 | 33.64 | 26.42 | 6385 |
| Example 9 | 28.12 | 33.72 | 26.42 | 8663 |
| Example 10 | 28.15 | 33.72 | 26.42 | 8663 |
| Example 11 | 28.12 | 33.70 | 26.43 | 8103 |
| Example 12 | 28.16 | 33.70 | 26.44 | 8103 |
| Example 13 | 28.12 | 33.68 | 26.42 | 7543 |
| Example 14 | 28.12 | 33.68 | 26.42 | 7543 |
| Example 15 | 28.12 | 33.60 | 26.42 | 5240 |
| Example 16 | 28.16 | 33.62 | 26.42 | 5815 |
| Example 17 | 28.16 | 33.60 | 26.42 | 5240 |
| Comparative Example 1 | 26.40 | 28.14 | 33.58 | 4667 |
| Comparative Example 2 | 28.14 | 33.77 | 26.42 | 10119 |
| Comparative Example 3 | 28.12 | 33.55 | 26.42 | 3809 |
| Comparative Example 4 | 28.12 | 33.53 | 26.42 | 3249 |
| Comparative Example 5 | 28.13 | 33.51 | 26.43 | 2651 |
| Comparative Example 6 | 28.12 | 33.50 | 26.42 | 2356 |
| Comparative Example 7 | 28.16 | 33.58 | 26.42 | 4667 |
| Comparative Example 12 | 26.42 | 28.14 | 33.55 | 3809 |

TABLE 3

| Number | isobutylene concentration % by volume | Reaction temperature °C. | Conversion rate % | methacrolein, selectivity % | methacrolein, yield % | methacrylic acid, selectivity % | methacrylic acid, yield % | Total, yield % | methacrolein, amount generated t |
|---|---|---|---|---|---|---|---|---|---|
| Example 1 | 8.0 | 430 | 95.5 | 85.6 | 81.7 | 1.9 | 1.6 | 83.4 | 30500 |
| Example 2 | 8.0 | 430 | 95.6 | 86.3 | 82.5 | 1.8 | 1.6 | 84.1 | 35200 |
| Example 3 | 8.0 | 430 | 95.6 | 86.5 | 82.7 | 1.9 | 1.6 | 84.3 | 35300 |
| Example 4 | 8.0 | 430 | 95.7 | 84.3 | 80.7 | 2.7 | 2.3 | 83.0 | 34400 |
| Example 5 | 8.0 | 430 | 95.6 | 84.9 | 81.2 | 2.2 | 1.9 | 83.0 | 33700 |
| Example 6 | 8.0 | 430 | 95.6 | 84.6 | 80.9 | 2.1 | 1.8 | 82.7 | 40300 |
| Example 7 | 8.0 | 430 | 95.7 | 84.0 | 80.4 | 2.7 | 2.3 | 82.7 | 37500 |
| Example 8 | 8.0 | 430 | 95.5 | 85.3 | 81.5 | 1.9 | 1.6 | 83.1 | 39300 |
| Example 9 | 8.0 | 430 | 95.5 | 83.5 | 79.7 | 2.8 | 2.3 | 82.1 | 30600 |
| Example 10 | 8.0 | 430 | 95.5 | 83.4 | 79.6 | 2.9 | 2.4 | 82.1 | 30500 |
| Example 11 | 8.0 | 430 | 95.6 | 83.8 | 80.1 | 2.8 | 2.3 | 82.5 | 38600 |
| Example 12 | 8.0 | 430 | 95.6 | 83.7 | 80.0 | 2.8 | 2.3 | 82.4 | 22100 |
| Example 13 | 8.0 | 400 | 95.5 | 83.6 | 79.8 | 2.9 | 2.4 | 82.3 | 38300 |
| Example 14 | 8.0 | 460 | 95.6 | 83.8 | 80.1 | 2.9 | 2.4 | 82.5 | 28900 |
| Example 15 | 8.0 | 430 | 95.6 | 83.5 | 79.8 | 3.1 | 2.6 | 82.4 | 28700 |
| Example 16 | 8.0 | 430 | 95.5 | 85.1 | 81.3 | 2.4 | 2.0 | 83.3 | 29300 |
| Example 17 | 8.0 | 430 | 95.5 | 84.6 | 80.8 | 2.8 | 2.4 | 83.2 | 29100 |
| Example 18 | 8.0 | 350 | 97.3 | 87.6 | 85.2 | 1.9 | 1.7 | 86.9 | 25600 |
| Example 19 | 8.0 | 480 | 95.6 | 86.0 | 82.2 | 2.0 | 1.7 | 83.9 | 29600 |
| Example 20 | 6.0 | 430 | 97.8 | 88.5 | 86.6 | 2.0 | 1.8 | 88.3 | 19500 |
| Example 21 | 6.0 | 350 | 97.8 | 88.1 | 86.2 | 1.8 | 1.6 | 87.7 | 19400 |
| Comparative Example 1 | 8.0 | 430 | 95.7 | 82.5 | 79.0 | 3.6 | 3.0 | 81.9 | 27100 |
| Comparative Example 2 | 8.0 | 430 | 95.6 | 82.3 | 78.7 | 3.0 | 2.5 | 81.1 | 26400 |
| Comparative Example 3 | 8.0 | 430 | 95.6 | 81.6 | 78.0 | 4.0 | 3.3 | 81.3 | 24400 |
| Comparative Example 4 | 8.0 | 430 | 95.6 | 77.5 | 74.1 | 4.4 | 3.4 | 77.5 | 21800 |
| Comparative Example 5 | 8.0 | 430 | 72.6 | 75.1 | 54.5 | 2.8 | 2.1 | 56.6 | 13300 |
| Comparative Example 6 | 8.0 | 430 | 95.6 | 74.3 | 71.0 | 3.8 | 2.8 | 73.9 | 22700 |
| Comparative Example 7 | 8.0 | 430 | 95.6 | 81.9 | 78.3 | 3.8 | 3.1 | 81.4 | 28200 |
| Comparative Example 8 | 8.0 | 350 | 95.6 | 80.1 | 76.6 | 3.5 | 2.8 | 79.4 | 22100 |
| Comparative Example 9 | 8.0 | 480 | 95.6 | 81.0 | 77.4 | 3.6 | 2.9 | 80.4 | 27900 |
| Comparative Example 10 | 6.0 | 430 | 95.3 | 82.2 | 78.3 | 3.9 | 3.2 | 81.5 | 14100 |
| Comparative Example 11 | 6.0 | 350 | 97.2 | 87.3 | 84.9 | 2.3 | 2.0 | 86.9 | 12700 |
| Comparative Example 12 | 8.0 | 430 | 95.6 | 82.9 | 79.3 | 3.1 | 2.6 | 81.8 | 27200 |

Example 22

The catalyst obtained in Example 1 was used, and as the reaction evaluation of the catalyst, a SUS reaction tube with a jacket having a diameter of 14 mm was filled with 4.0 g of the catalyst. A mixed gas containing 8% by volume of t-butyl alcohol, 12.8% by volume of oxygen, 3.0% by volume of water vapor, and 76.2% by volume of nitrogen was aerated in a flow rate of 120 mL/min (NTP) at a reaction temperature of 430° C., to carry out a methacrolein synthetic reaction. The reaction evaluation results are shown in Table 4.

Comparative Example 12

The catalyst obtained in Comparative Example 1 was used, and as the reaction evaluation of the catalyst, a reaction tube was filled with 4.2 g of the catalyst. A methacrolein synthetic reaction was carried out under the same reaction condition as that of Example 22. The reaction evaluation results are shown in Table 4.

TABLE 4

| Number | t-butyl alcohol concentration, % by volume | Reaction temperature ° C. | Conversion rate % | methacrolein, selectivity % | methacrolein, yield % | methacrylic acid, selectivity % | methacrylic acid, yield % | Total, yield % | methacrolein, amount generated t |
|---|---|---|---|---|---|---|---|---|---|
| Example 22 | 8.0 | 430 | 95.5 | 83.5 | 79.7 | 2.0 | 1.7 | 81.4 | 28700 |
| Comparative Example 13 | 8.0 | 430 | 95.6 | 80.5 | 77.0 | 3.3 | 2.7 | 79.6 | 26400 |

Example 23

The catalyst obtained in Example 1 was used, and a SUS reaction tube with a jacket having an inner diameter of 15 mm was filled with 20 mL of the catalyst. A starting material gas having a propylene concentration of 10% by volume, a water vapor concentration of 17% by volume, and an air concentration of 73% by volume was passed for a contact time of 2.3 seconds under normal pressure, to carry out an acrolein synthetic reaction at a reaction temperature of 430° C. The reaction evaluation results are shown in Table 5.

Comparative Example 13

The catalyst obtained in Comparative Example 1 was used, and a reaction tube was filled with 20 mL of the catalyst. An acrolein synthetic reaction was carried out under the same reaction condition as that of Example 23. The reaction evaluation results are shown in Table 5.

As apparent from the above-mentioned reaction evaluation results, the oxide catalyst according to the present embodiment caused less generation of the successive oxide in the oxidation reaction of the olefin and/or the alcohol, and could enhance the selectivity of the unsaturated aldehyde.

The present application is based on the Japanese patent application filed on Jun. 28, 2011 (Japanese Patent Application No. 2011-143284), whose contents are hereby incorporated by reference herein.

INDUSTRIAL APPLICABILITY

The oxide catalyst according to the present invention can be industrially utilized as the catalyst used in the oxidation reaction of the olefin and/or the alcohol.

The invention claimed is:

1. An oxide catalyst for use in an oxidation reaction of an olefin and/or an alcohol, the oxide catalyst comprising: molybdenum, bismuth, iron, cobalt, and cerium; an atomic ratio a of bismuth to 12 atoms of molybdenum is $2 \leq a \leq 6$, an atomic ratio b of iron to 12 atoms of molybdenum is $2.5 < b \leq 5$, an atomic ratio c of cobalt to 12 atoms of molybdenum is $2 \leq c \leq 8$, an atomic ratio d of cerium to 12 atoms of molybdenum is $0.5 \leq d \leq 6$, and an atomic ratio of iron/cobalt is $0.4 \leq b/c \leq 2.5$;

wherein when a spacing d of a complex oxide of cerium and molybdenum showing a peak at 33.50° in a X-ray diffraction is taken as a reference, a change rate of d is 5000 to 9000 ppm.

2. The oxide catalyst according to claim 1, wherein the oxide catalyst comprises a composition represented by formula (1):

$$Mo_{12}Bi_aFe_bCo_cCe_dA_eB_fO_g \qquad (1),$$

wherein Mo represents molybdenum; Bi represents bismuth; Fe represents iron; Co represents cobalt; Ce represents cerium; A represents at least one element selected from the group consisting of cesium and rubidium; B represents at least one element selected from the group consisting of copper, nickel, magnesium, and lead; a to f represents an atomic ratios of each element to 12 atoms of Mo; $2 \leq a \leq 6$, $2.5 < b \leq 5$, $2 \leq c \leq 8$, $0.4 \leq b/c \leq 2.5$, $0.5 \leq d \leq 6$, $0.01 \leq e \leq 2$, and $0 \leq f < 2$ are satisfied; and g represents a number of oxygen atoms determined by a valence of a constituent element other than oxygen.

TABLE 5

| Number | propylene concentration, % by volume | Reaction temperature ° C. | Conversion rate % | acrolein, selectivity % | acrolein, yield % | acrylic acid, selectivity % | acrylic acid, yield % | Total, yield % | acrolein, amount generated t |
|---|---|---|---|---|---|---|---|---|---|
| Example 23 | 10.0 | 430 | 98.9 | 94.0 | 93.0 | 2.4 | 2.3 | 95.2 | 33500 |
| Comparative Example 14 | 10.0 | 430 | 98.9 | 93.3 | 92.3 | 2.9 | 2.7 | 95.0 | 33200 |

3. A method for producing the oxide catalyst according to claim 1 or 2, the method comprising the steps of:
aging a starting material slurry comprising molybdenum, bismuth, iron, cobalt, and cerium at a temperature higher than room temperature;

drying the aged starting material slurry;
preliminarily calcining the dried product at 120° C. or more and 350° C. or less; and
subsequently finally calcining the preliminarily calcined product at a temperature of 400° C. or more and 700° C. or less.

4. A method for producing an unsaturated aldehyde comprising the step of oxidizing at least one olefin selected from the group consisting of propylene and isobutylene and/or t-butyl alcohol using the oxide catalyst according to claim 1 or 2.

* * * * *